US008956285B2

(12) United States Patent
Gephart et al.

(10) Patent No.: US 8,956,285 B2
(45) Date of Patent: Feb. 17, 2015

(54) RETRACTION APPARATUS AND METHOD OF USE

(75) Inventors: Matthew P Gephart, Marquette, MI (US); Phillip J. Berman, Negaunee, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 1470 days.

(21) Appl. No.: 12/161,944

(22) PCT Filed: Jan. 23, 2007

(86) PCT No.: PCT/US2007/060925
§ 371 (c)(1),
(2), (4) Date: Sep. 11, 2008

(87) PCT Pub. No.: WO2007/087536
PCT Pub. Date: Aug. 2, 2007

(65) Prior Publication Data
US 2009/0069635 A1 Mar. 12, 2009

Related U.S. Application Data

(63) Continuation-in-part of application No. 11/539,224, filed on Oct. 6, 2006, now Pat. No. 7,985,179.

(60) Provisional application No. 60/761,559, filed on Jan. 23, 2006.

(51) Int. Cl.
*A61B 17/02* (2006.01)
*A61B 1/32* (2006.01)

(52) U.S. Cl.
CPC . *A61B 1/32* (2013.01); *A61B 17/02* (2013.01); *A61B 17/025* (2013.01); *A61B 17/0293* (2013.01)

USPC .......................... 600/224; 600/215; 600/222

(58) Field of Classification Search
USPC ......... 600/204, 210, 214–216, 219–222, 224, 600/225, 227, 201, 231–233
See application file for complete search history.

(56) References Cited

U.S. PATENT DOCUMENTS 2,473,266 A 6/1949 Wexler
2,623,517 A 12/1952 Barlow et al.
(Continued)

FOREIGN PATENT DOCUMENTS

WO 03086202 10/2003
WO 2004047650 10/2004
(Continued)

OTHER PUBLICATIONS

SynFrame Access and Retractor System Assembly Guide, SYNTHES Spine, assembly guide provided by the manufacturer, 1999, 12 pages, Paoli, Pennsylvania.
(Continued)

*Primary Examiner* — Michael T Schaper
(74) *Attorney, Agent, or Firm* — Fitch, Even, Tabin & Flannery, LLP

(57) ABSTRACT

A retraction apparatus and method are disclosed that provide optimized access to a surgical site. In one form, a retraction frame has a retraction opening with two sets of blades operating therein. The blades are used to sequentially retract the tissue from about an incision. The sequential retraction of the blades generates only narrow gaps between the blades so that tissue and blood encroachment during the surgical procedure are minimized.

17 Claims, 27 Drawing Sheets

(56) References Cited

U.S. PATENT DOCUMENTS

| | | | |
|---|---|---|---|
| 3,038,468 A | 6/1962 | Raeuchle | |
| 3,724,449 A | 4/1973 | Gauthier | |
| 3,948,259 A | 4/1976 | Bolduc et al. | |
| 3,998,217 A | 12/1976 | Trumbull et al. | |
| 4,010,741 A | 3/1977 | Gauthier | |
| 4,434,791 A | 3/1984 | Darnell | |
| 5,667,481 A | 9/1997 | Villalta et al. | |
| 5,688,223 A * | 11/1997 | Rosendahl | 600/215 |
| 5,728,046 A | 3/1998 | Mayer et al. | |
| 5,813,978 A | 9/1998 | Jako | |
| 5,928,139 A | 7/1999 | Koros et al. | |
| 5,944,658 A * | 8/1999 | Koros et al. | 600/232 |
| 5,954,635 A | 9/1999 | Foley et al. | |
| 5,957,927 A | 9/1999 | Magee et al. | |
| 5,967,973 A | 10/1999 | Sherts et al. | |
| 6,083,154 A | 7/2000 | Liu et al. | |
| 6,139,493 A | 10/2000 | Koros et al. | |
| 6,206,826 B1 | 3/2001 | Mathews et al. | |
| 6,213,940 B1 | 4/2001 | Sherts et al. | |
| 6,224,545 B1 | 5/2001 | Cocchia et al. | |
| 6,322,500 B1 | 11/2001 | Sikora et al. | |
| 6,416,467 B1 | 7/2002 | McMillin et al. | |
| 6,464,634 B1 | 10/2002 | Fraser | |
| 6,616,605 B2 | 9/2003 | Wright et al. | |
| 6,800,084 B2 | 10/2004 | Davison et al. | |
| 6,849,064 B2 | 2/2005 | Hamada | |
| 6,869,398 B2 | 3/2005 | Obenchain et al. | |
| 6,896,654 B2 | 5/2005 | Paolitto et al. | |
| 6,932,764 B2 | 8/2005 | Kashyap | |
| 7,195,592 B2 | 3/2007 | Ravikumar et al. | |
| 7,780,594 B2 | 8/2010 | Hutton | |
| 2002/0111538 A1 * | 8/2002 | Wright et al. | 600/233 |
| 2002/0193666 A1 | 12/2002 | Sherts et al. | |
| 2003/0191371 A1 | 10/2003 | Smith et al. | |
| 2004/0002629 A1 | 1/2004 | Branch et al. | |
| 2004/0059193 A1 * | 3/2004 | Fanous | 600/220 |
| 2004/0087833 A1 | 5/2004 | Bauer | |
| 2004/0133077 A1 * | 7/2004 | Obenchain et al. | 600/224 |
| 2004/0133201 A1 | 7/2004 | Shluzas et al. | |
| 2004/0176665 A1 | 9/2004 | Branch | |
| 2004/0193018 A1 | 9/2004 | Thalgott et al. | |
| 2004/0230100 A1 | 11/2004 | Shluzas | |
| 2004/0242969 A1 | 12/2004 | Sherts et al. | |
| 2005/0080320 A1 | 4/2005 | Lee et al. | |
| 2005/0137461 A1 | 6/2005 | Marchek et al. | |
| 2005/0149035 A1 | 7/2005 | Pimenta et al. | |
| 2005/0159650 A1 | 7/2005 | Raymond et al. | |
| 2005/0159651 A1 | 7/2005 | Raymond et al. | |
| 2005/0192485 A1 | 9/2005 | Branch et al. | |
| 2005/0215862 A1 | 9/2005 | Larson et al. | |
| 2005/0215866 A1 | 9/2005 | Kim | |
| 2005/0234304 A1 | 10/2005 | Dewey et al. | |
| 2005/0261694 A1 | 11/2005 | Orton et al. | |
| 2005/0277812 A1 | 12/2005 | Myles | |
| 2006/0004261 A1 | 1/2006 | Douglas | |
| 2006/0030858 A1 | 2/2006 | Simonson et al. | |
| 2006/0052672 A1 * | 3/2006 | Landry et al. | 600/233 |
| 2006/0074445 A1 | 4/2006 | Gerber et al. | |
| 2007/0118022 A1 | 5/2007 | Hutton | |
| 2007/0156025 A1 | 7/2007 | Marchek et al. | |
| 2007/0161867 A1 | 7/2007 | Fowler, Jr. et al. | |
| 2007/0203399 A1 | 8/2007 | Gephart et al. | |
| 2007/0238932 A1 | 10/2007 | Jones et al. | |
| 2007/0282171 A1 | 12/2007 | Karpowicz et al. | |

FOREIGN PATENT DOCUMENTS

| | | |
|---|---|---|
| WO | 2005092206 | 6/2005 |
| WO | 2005094695 | 10/2005 |
| WO | 2005096735 | 10/2005 |

OTHER PUBLICATIONS

ProAccess™ Radiolucent Retractor Blades, SYNTHES Spine, product offerings guide provided by the manufacturer, 2004, 2 pages, Paoli, Pennsylvania.

Webb, J., Spine-The Future, AO Foundation Webpage, available at: http://www.aofoundation.org/AOFileServer/PortalFiles?FilePath=/Extranet2007/active/_att/wor/act/Dialogue/1999_2/spine.pdf, accessed Apr. 10, 2009.

United States Patent and Trademark Office, Non-Final Office Action mailed Oct. 15, 2009 in related U.S. Appl. No. 11/539,224 (17 pages). Amendment filed Apr. 14, 2010, in related U.S. Appl. No. 11/539,224 (25 pages).

United States Patent and Trademark Office, Final Office Action mailed Jul. 7, 2010 in related U.S. Appl. No. 11/539,224 (15 pages). Amendment filed Dec. 6, 2010, in related U.S. Appl. No. 11/539,224 (14 pages).

An International Search Report dated Nov. 29, 2007, from the International Bureau in corresponding International (PCT) Application No. PCT/US07/60925.

* cited by examiner

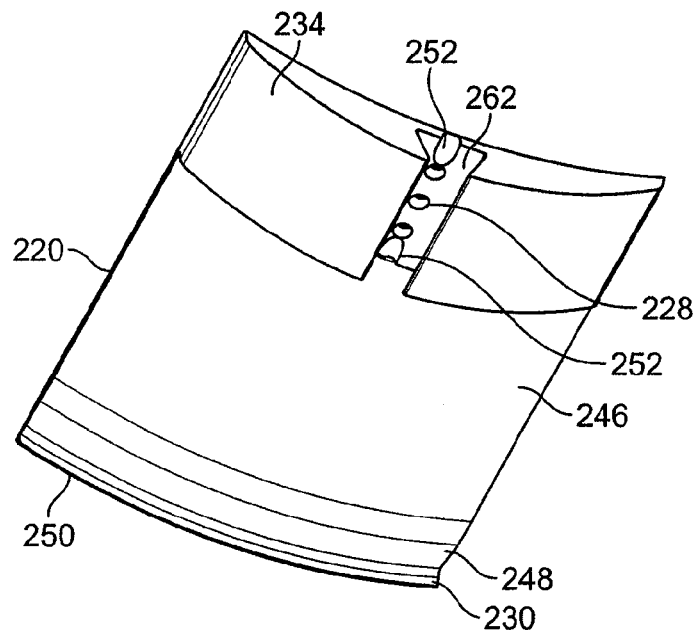
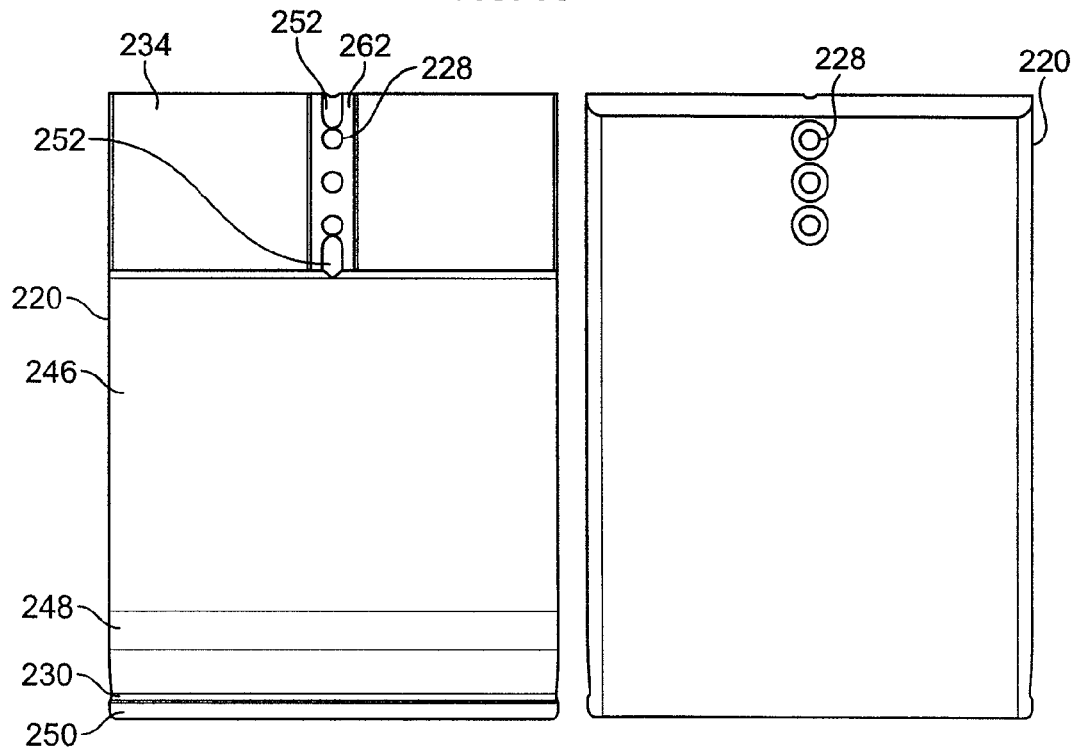
FIG. 30
FIG. 31                    FIG. 32

RETRACTION APPARATUS AND METHOD OF USE

CROSS-REFERENCE TO RELATED APPLICATIONS

This application is a U.S. National Stage application of International Application No. PCT/US2007/60925, filed Jan. 23, 2007, which is a continuation-in-part of U.S. Utility Application No. 11/539,224, filed Oct. 6, 2006, which claims the benefit of U.S. Provisional Application No. 60/761,559, filed on Jan. 23, 2006, which are hereby incorporated herein by reference in their entirety.

FIELD OF THE INVENTION

The invention relates generally to a retractor and method for providing access to a surgical site and, more particularly, a retractor and method for retracting tissue during a surgical procedure.

BACKGROUND OF THE INVENTION

While incisions are required during surgical procedures to gain access to the surgical site, such incisions can cause damage, injury, and trauma to the patient's body. To avoid causing unnecessary damage, it is preferable to make the incisions as small as possible, while retaining a clear view of the surgical site. Retractors are used to maximize the viewing range of incisions, thereby allowing the surgeon to minimize damage.

In addition, retractors are used to keep the incision open and provide a clear view of the operating site during the procedure. Retractors can be used to relocate various types of tissue, nerves, bone, cartilage, and ligaments. Such repositioning is often accomplished by employing tissue engaging members or blades that reposition and retain the tissue and other bodily substances in the adjusted position thereby providing clearance to the surgical site.

A significant problem with retractors currently used during surgical procedures, is that after the blades are moved from the unretracted position to the retracted position, the blades are spaced significantly apart. The space between the retractor blades allows tissue, and blood to encroach upon the surgical site. The gaps can become increasingly problematic throughout the procedure.

Accordingly, there is a need for an access retractor that repositions tissue and blood from a surgical site and minimizes tissue encroachment throughout the duration of the surgical procedure.

SUMMARY OF THE INVENTION

In accordance with one aspect of the present invention, access retraction apparatus and methods are disclosed that provide optimized access to a surgical site through an incision during a surgical procedure. To this end, the apparatus and methods utilize tissue engagement members, such as in the form of retractor blades. The retractor blades are operable to pull tissue about the incision apart while substantially minimizing tissue and blood encroachment into the surgical site during surgical procedures. The preferred retractor includes a frame or body having a retraction opening in which the retractor blades are operable to provide optimized access to the surgical site by keeping tissue encroachment beyond the retracted blades to a minimum. Sets of opposing blades are provided, including a set having a narrow width and a set having a comparatively wide width. Operating mechanisms for the blades are configured to allow for sequential retraction of the sets of blades which, in turn, allow for gaps between the blades to be minimized in size.

In one form, the narrow width blade set is initially retracted in a first direction. The wide width blade set can then be inserted into the enlarged opening and retracted to further enlarge the opening in a second direction transverse, and preferably perpendicular, to the first direction in order to retract the tissue to form an oblong opening surrounded by the blades. The use of two different blade widths and the sequential use of those blades permits the gaps between adjacent blades to be minimized to reduce encroachment of tissue through the gaps.

Before the access retraction apparatus is employed, an incision is made into the patient's body where access for surgical instruments through an incision into a patient's body is desired. After making the incision, the access retractor may be utilized with the two narrower blades in their fully extended, unretracted position, closely adjacent one another. By first using the narrower blade set for retraction prior to the wider blades, the size of the incisions can be kept to a minimum. Alternatively, a harpoon dilator or number of cannulated tools can be used to stretch the skin, after which the blades of one of the blade sets of the access retractor are inserted over the dilation tool. In this regard, the blades can be retracted to an intermediate position between fully retracted and fully extended relative to the retraction opening so that the blades are sufficiently spaced to allow them to be positioned in a close fit around the dilation tool.

Each of the blades is preferably removably attached to a slider mechanism to allow for shifting of the blades to different positions. The set of narrower blades, which retract first, preferably have a ratcheting slider mechanism that provides retraction over small increments. This provides numerous closely spaced, predetermined retraction positions for the narrow blades. Subsequently, the wide blades are retracted. The wide blades can be selected from a plurality of different widths. In one aspect, the wide blades have only two positions, retracted and extended. In another aspect, the wide blades also use a ratcheting slider mechanism that provides retraction over small increments. The width of the wide blades used is limited by how far the narrower blades were retracted in the first or initial stage of retraction. Substantially matching the width of the wide blades to the distance traveled by the narrow blades during the first retraction stage ensures that minimal space will be available between the blades for tissue encroachment. In addition to allowing for different sizes of blades to be interchanged, and in particular for the blades of the wide blade set used with the retractor, the detachable connections also enable the blades and slider mechanisms to more easily be cleaned and sanitized.

To move the blades between the different retraction positions, a spreading instrument can be employed. The spreading instrument may include a pair of connecting arms which guide the retraction movement between the frame and the blade. When retracting the blades, the connecting arms are rigidly connected to attachment structure such as in the form of pegs, cylinders, or holes on the frame and sliders. After the blades have been moved to the retracted position, the slider mechanism locks into place and the spreading instrument can be removed. The spreading instrument may comprise a lamina spreader that is used to simultaneously retract opposing blades.

In one form, the retractor opening is generally oblong, i.e., having a length that is substantially greater than its width. However, in another form the retractor opening has a length that is close to or about the same as its width. The opening can have a variety of shapes, such as generally circular, ovoid, rectangular, or square. For generally rectangular or square openings, the inner corners are slightly curved so that radii thereof are kept to a minimum to provide for increased area of the opening, and thus increased access space for the surgeon. Depending upon the shape and size of the retractor opening, the retractor can accommodate four blades of relatively equal width or blades having multiple widths. Increasing the area of the opening can provide the surgeon with flexibility such that different patients and procedures can more easily be accommodated.

In yet another form, the frame or body of the retractor may have positions or sections that are adjustable relative to each other, such as by pivoting. In this regard, the retractor frame has at least one articulating section. This section may be hingedly or pivotally attached or otherwise moveably attached to the remainder of the frame and may be releasably fixable relative to the remainder of the frame. A retractor with such articulation capabilities can move from a relatively planar profile to a profile that more closely corresponds to the contours of the patient's body, to allow for ease of insertion into the underlying incision. With more precise positioning of the retractor relative to the tissue surrounding the incision, the retractor can provide better access to the surgical site and reduce the stress and trauma to the patient, and more particularly, the surgical site and the tissue adjacent thereto. Such an articulating section may include a set of pivot connections on the retractor frame. In one embodiment, the pivot connections are hinges located on either side of the retractor frame. In another embodiment, two or more articulating sections may be provided.

Since the blades, whether wide, medium, or narrow width, can be retracted to a large number of different positions, the access retractor can be used for many different surgical procedures and for different patients. The primary use for the access retractor illustrated herein will be for use during a surgical procedure requiring access to the lumbar spinal region.

BRIEF DESCRIPTION OF THE DRAWINGS

FIG. 11 is a side elevational view of the spreading instrument similar to

FIG. 10 showing the actuator arms shifted apart and in parallel orientation relative to each other.

FIG. 30 is a rear perspective view of one of the second set of blades of FIG. 19;

FIG. 31 is a rear elevation view of the blade of FIG. 30;

FIG. 32 is a front elevation view of the blade of FIG. 30;

DETAILED DESCRIPTION OF THE PREFERRED EMBODIMENTS

Access retractors are illustrated in FIGS. 1-32 and 34-35 for use in enlarging a surgical incision for a surgical procedure, and in particular for stretching the tissue surrounding the incision. The access retractors use multiple stages of retraction of a plurality of tissue engaging members in order to minimize gaps between the tissue engaging members to advantageously reduce the encroachment of tissue, fluid and other matter through the gaps. More specifically, a first, narrow set of tissue engaging members are inserted into the incision and moved from an extended position toward a retracted position using the access retractor in order to stretch the incision to an intermediate size opening. Next, a second, wider set of tissue engaging members are inserted into the intermediate size opening and moved from an extended position toward a retracted position to stretch the intermediate size opening to a final size opening. The sequential use of two different sets of tissue engaging members, each having a different width, can result in an oblong opening bounded by the tissue engaging members having minimal gaps between adjacent ones of the tissue engaging members, in particular as compared to using equal width tissue engaging members.

Figure 1:
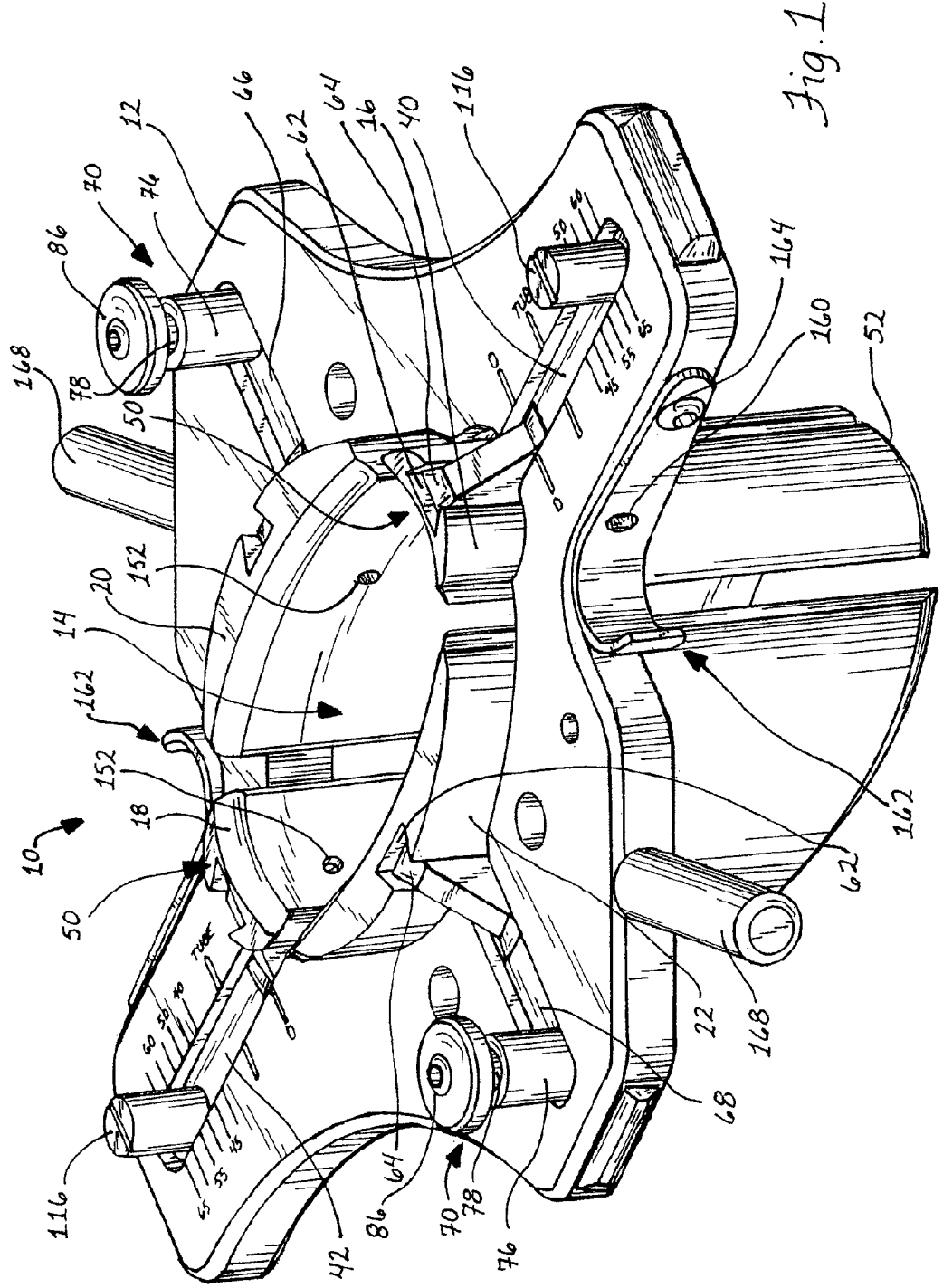
FIG. 1 is a perspective view of a first embodiment of an access retractor in accordance with the present invention shown with first and second sets of blades in the fully retracted position.

In FIG. 1, a first embodiment of an access retractor generally designated 10 is depicted in the fully retracted or open position thereof. The retractor 10 includes a frame or body 12 having a large retraction opening 14 centrally located for viewing the surgical site. Inside the viewing window 14 are located a number of tissue engaging members, such as in the form of retraction blades 16, 18, 20, and 22. To keep gaps between adjacent, retracted blades to a minimum, it is preferred to undertake the retraction procedure in different stages so that retraction of an incision occurs sequentially with the preferred retractor 10 described herein. In the illustrated and preferred form, it is the narrower blades 16 and 18 disposed opposite from each other across the retraction opening 14 that are retracted during the first or initial stage of the retraction procedure and the wider blades 20 and 22 disposed opposite from each other across the retraction opening 14 that are retracted during the second or final stage of the retraction procedure. The sequential use of narrow blades 16, 18 and wide blades 20, 22 can advantageously result in an enlarged opening substantially surrounded by the blades 16, 18, 20 and 22, with reduced gaps between adjacent ones of the blades 16, 18, 20 and 22 to minimize encroachment of tissue and other matter through the gaps.

More generally, the first retraction stage involves retracting the blades 16 and 18 in a direction 24 that is transverse to the direction 26 in which the blades 20 and 22 are retracted in the second stage. In this manner, the blades 20 and 22 can be sized to be larger than the blades 16 and 18 since these blades 16 and 18 have already been used to expand the size of the incision into which they extend to form an opening 30 that generally has an enlarged size in the direction 24 of retraction.

Figure 3:
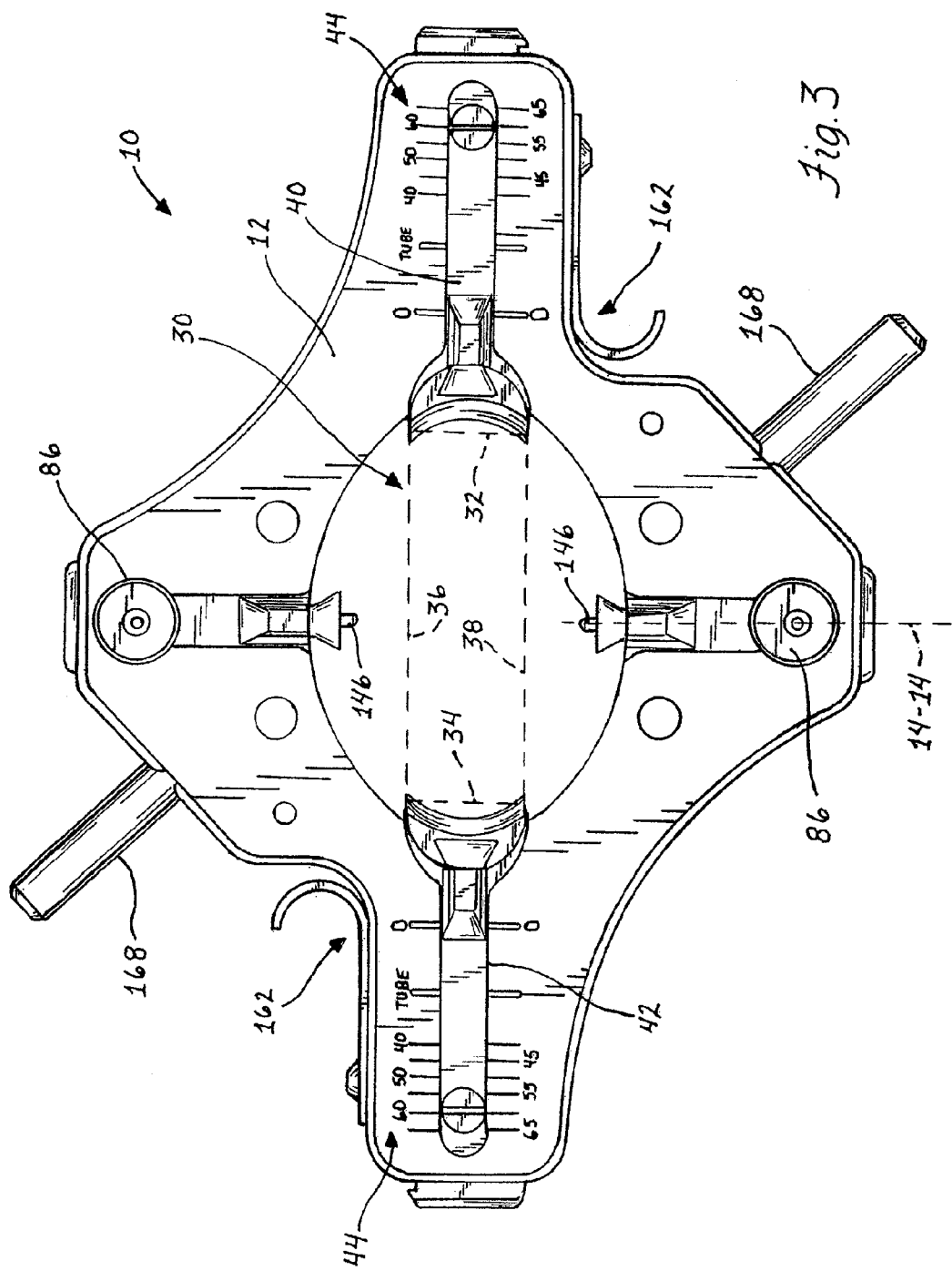
FIG. 3. is a bottom plan view of the access retractor shown with the first set of blades in the full retracted position, and the second set of blades removed from the retractor.

Referring to FIG. 3, the opening 30 may take on a generally rectangular configuration with the width of the blades 16 and 18 generally defining the size of the opposite short sides 32 and 34 of the rectangular opening 30. The position that the narrower blades 16 and 18 are retracted to will define the size of the opposite long sides 36 and 38 of the rectangular opening 30. In other words, the distance the narrow blades 16 and 18 are spaced from each other across the rectangular incision opening 30 after the initial stage of the retraction procedure will generally define the length of the long sides of the rectangular opening 30. The size of the rectangular sides limits the width of the blades 20 and 22 that can be fit within the opening 30 for undertaking the next stage of the retraction procedure. Nevertheless, it can be seen that the width size of those blades 20 and 22 in the longitudinal retraction direction 26 of blades 20 and 22 are generally aligned with the orientation of the long sides 36, 38 of the opening 30 and can be larger than the blades 16 and 18.

Thus, the blades can be provided in sets so that there is a narrow blade set including the blades 16 and 18 and a wider blade set including the blades 20 and 22. Because the blades 16 and 18 can be retracted to a large number of different positions as will be described in more detail hereinafter, the blades 20 and 22 can be provided in a number of differently sized wide blade sets for fitting in the opening 30 depending on its size as determined by how far the blades 16 and 18 are retracted apart from each other. Accordingly, while the narrow blade set can include a single width size of narrow blades 16 and 18, the wide blade set preferably includes several different width sizes of wide blades 20 and 22. Manifestly, the retractor 10 herein can be used with blades and sets of blades in a wide variety of numbers and sizes, not limited by the preferred arrangement described therein.

Figure 2:
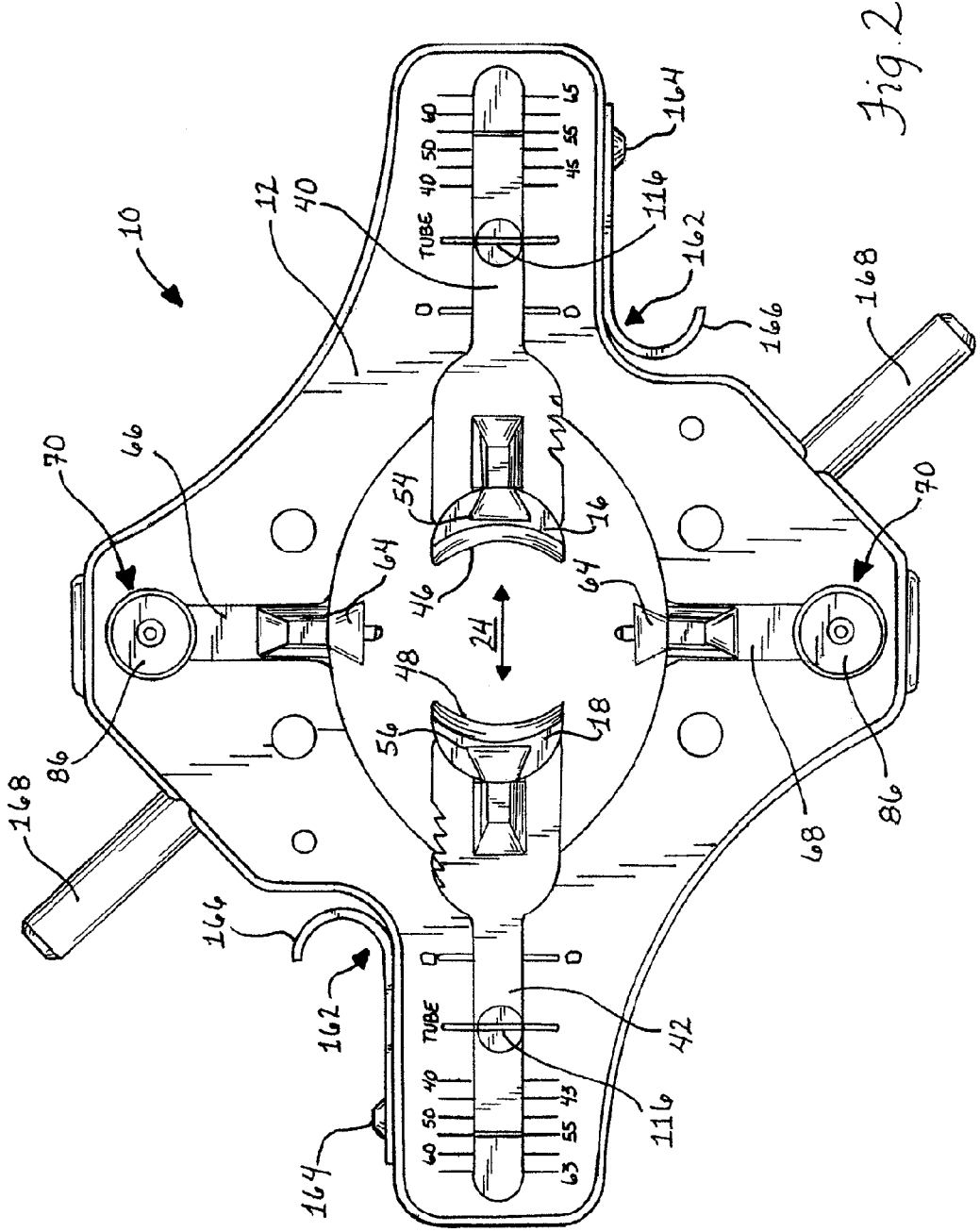
FIG. 2 is a bottom plan view of the access retractor shown with the first set of blades in an intermediate position for use with a tubular dilator tool.

The narrow retraction blades 16 and 18 are attached to slider mechanisms 40 and 42 that shift the blades between an intermediate position (FIG. 2) to the retracted position (FIG. 3). The access retractor 10 can be used immediately after the incision is made into the body. This requires that the slider mechanisms 40 and 42 be in the completely extended or unretracted position. Alternatively, a generally tubular dilation tool can be used to stretch the skin about the incisions before employing the retractor. In that situation, the slider mechanisms 40 and 42 are retracted to a predetermined, intermediate position as indicated by the "tube" setting on scale 44 for the slider mechanisms 40, 42 of the narrow blades. In this position, the blades are sufficiently spaced apart so that the arcuate facing surfaces 46 and 48 of the opposite blades can slide around the tubular tool. FIG. 2 illustrates the tube configuration of the tool.

The narrow blades 16 and 18 each have an upper attachment end 50 that attaches the blades 16, 18 to the retractor, and specifically the slider mechanisms mounted thereto, and a lower insertion end 52 that extends into the incision. After the retraction frame 12 and sliders 40, 42 have been positioned over the incision, the insertion ends 52 of the narrow blades 16 and 18 can be slid into the incision and the attachment ends 50 can be attached to the sliders 40 and 42.

Each of the blades is attached to the slider mechanisms by a dovetail connection 54, 56, 58, and 60. More specifically, narrow blades 16 and 18 have dovetail recesses 62, and the sliders 40 and 42 have dovetail projections 64 sized for a sliding fit in the corresponding recesses 62. As will be discussed further below, the dovetail connections 54, 56, 58 and 60 allows for the removal of the blades.

In the preferred form, the sliders 40 and 42 are ratcheting sliders allowing for small discrete movements of the narrow blades 16 and 18. Preferably, the narrow sliders 40 and 42 can be shifted to several different predetermined positions from "0" at the fully extended position in the retractor opening 14 with the blades 16 and 18 at the closest position to each other to "65 mm" at the fully retracted position in the retractor opening 14 with the blades 16 and 18 at their furthest position spaced apart from each other. More specifically, the blades have a full extended position at "0" for use where no dilation tool is employed prior to use of the retractor. If a dilation tool is present in the incision, then the "TUBE" setting can be used to space the blades 16 and 18 from each other across the opening 14 so that the respective arcuate, inner surfaces 46, 48 thereof can slide down along the outer cylindrical surface as defined by the circle of FIG. 2 of the tool in close fit therewith. This "TUBE" setting is for a specific diameter dilation tool. Manifestly, this setting can be implemented by providing at different positions along the scale 44 depending on the tool diameter. Regardless of the starting position, the sliders 40, 42 and associated blades 16, 18 can be retracted from this position to positions where the blades 16, 18 are spaced 40 mm from each other across the opening 14 by 5 mm increments up to the fully retracted position where the blades 16, 18 are spaced 65 mm from each other across the opening 14. As shown in FIG. 3, the narrow blades, 16 and 18 have been retracted to the 60 mm spaced apart position.

After this initial stage of the retraction procedure, the sliders 66 and 68 for the respective wide blades 20 and 22 are shifted to their extended positions in the retractor opening, and the appropriately sized wide blades 20 and 22 are selected and attached thereto to fit into the rectangular opening 30 formed by the retracted narrow blades 16 and 18, as described earlier. Preferably, the narrow slides can be shifted at increments of 2.5 mm, as can be seen by the scale 44 on retractor 10 shown in FIGS. 1-3 and 5-7. Other incremental movements, such as 3.25 mm, are contemplated.

Similar to the narrow blades 16 and 18, the wide blades 20 and 22 are attached to the sliders 66 and 68 by a pair of dovetail connections 58 and 60. Before the wide blades 20, 22 are attached the blade length must be chosen, as mentioned above. The wide blades can be provided in any number of sizes. By way of example, three sizes of wide blades can be provided. A wide blade with a width of 32 mm is used for a narrow blade retraction between 40 and 49 mm. A wide blade width of 42 mm is used for a narrow blade retraction between 50 and 59 mm. Finally, a wide blade width of 52 mm is used for a narrow blade retraction between 60 and 69 mm.

Figure 4:
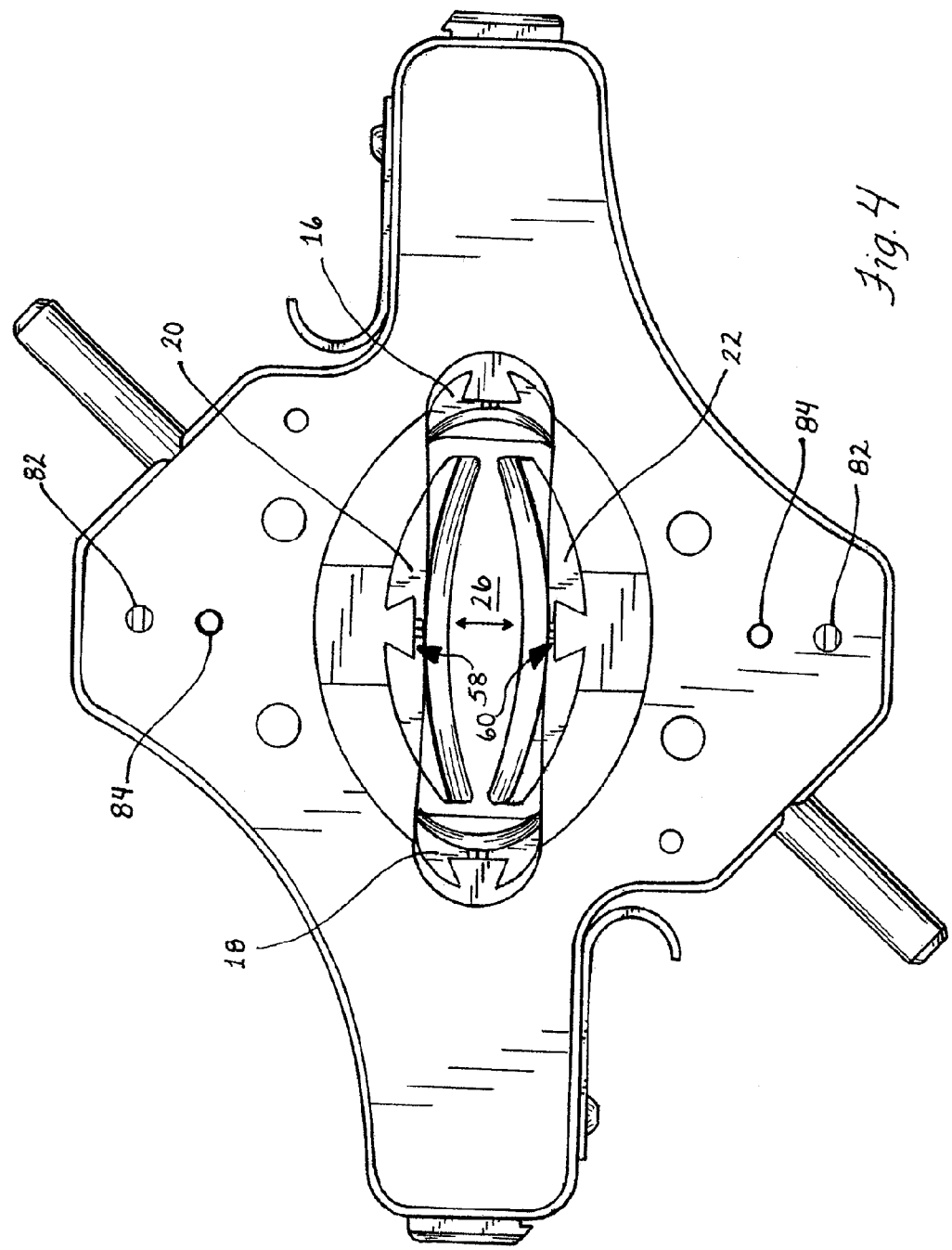
FIG. 4 is a bottom plan view of the access retractor shown with the first set of blades in the retracted position and with the second set of blades attached to the retractor in the first extended position.

As mentioned, the wide blades 20 and 22 may be provided with only two positions via their respective slide mechanisms 66 and 68, an extended position and a retracted position in the retractor opening. A spring loaded plunger assembly 70 is carried with each of the sliders 66, 68. A coil spring 72 is mounted in a downwardly opening pocket 74 of a fixed sleeve member 76 of the plunger assembly 70 through which a plunger member 78 extends. The fixed member 76 is fixed to the slider 66, or 68 toward its lower end. The spring 72 biases the distal end 80 of the plunger member 78 of the plunger assembly 70 out of the pocket 74 into one of the two openings 82 and 84 which are linearly aligned in the retraction direction 26 along which the sliders are shifted. To shift the slider, a surgeon simply pulls on disc handle 86 connected at the proximate end of the plunger member 78 to lift the distal end 80 out of the opening 82 or 84 aligned therewith and into the pocket 74 so that the slider 66, 68 can then be shifted until the plunger end 80 is aligned with the other opening 82 or 84. The bias force provided by the spring 72 causes the end 80 to snap into the aligned opening 82 or 84 for releasably locking the slider in the desired position. The two openings 82 and 84 correspond to the extended position and the retracted position of the wide blades 20 and 22. After the initial stage narrow blade retraction procedure, the wide blade sliders 66 and 68 are shifted to the extended position. The wide blades 20 and 22 are then slid down onto the sliders 66 and 68, respectively, for being attached thereto via the dovetail connections 58 and 60 therebetween, as shown in FIG. 4.

Sliding the wide blades 20 and 22 down along the dovetail projections 64 inserts the blades 20 and 22 into the rectangular opening 30 of the incision. The blades 20 and 22 and associated sliders 66 and 68 have a releasable connection 90 therebetween that is operable when the blades 20 and 22 slide down to a predetermined position relative to the sliders 66 and 68. The releasable connection 90 is shown best in FIGS. 12 and 13 and will be described in more detail hereinafter.

Figure 5:
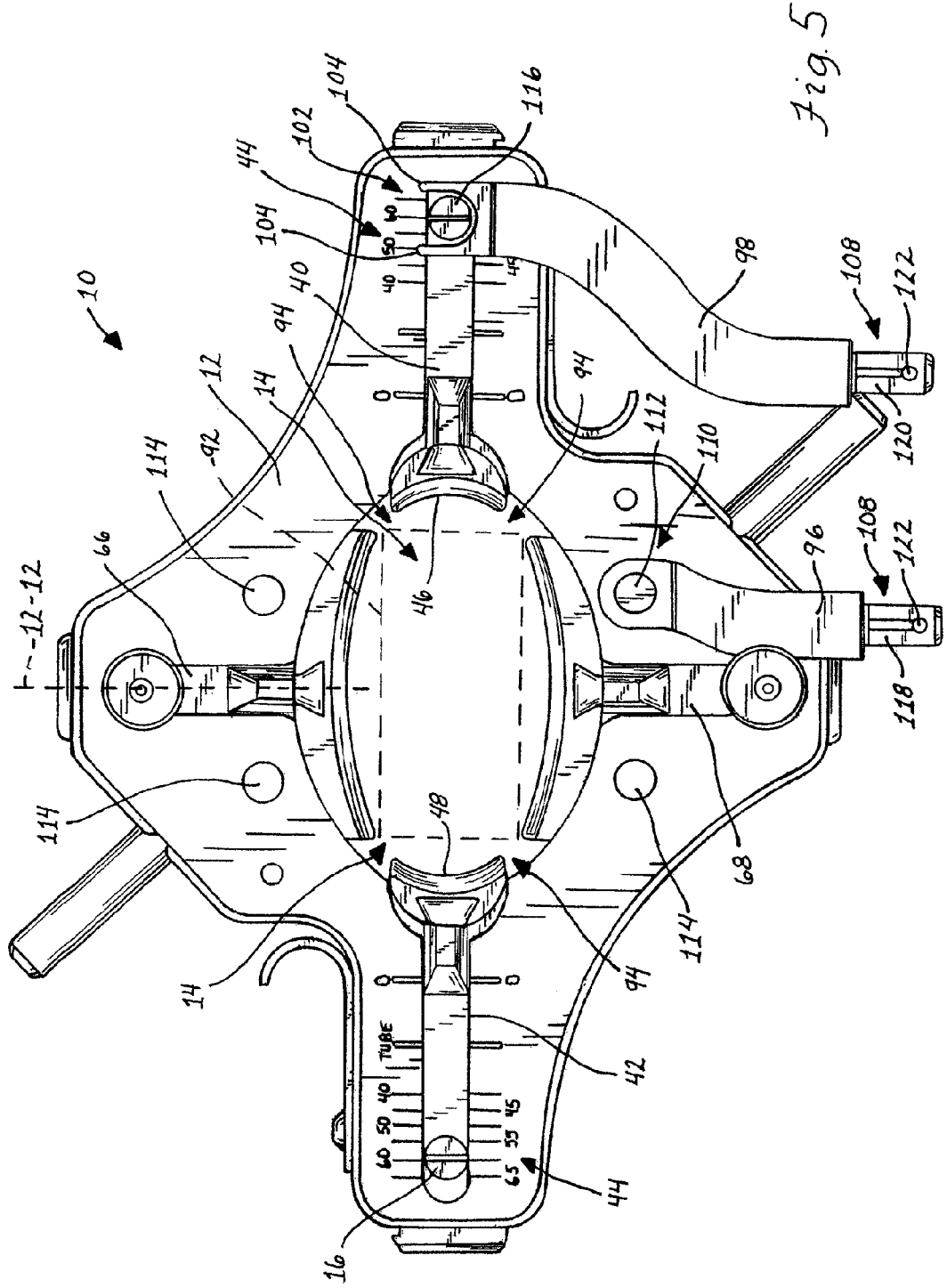
FIG. 5 is a bottom plan view of the access retractor showing the first and second sets of blades in the full retracted positions and a pair of connecting arms attached to a frame of the retractor and one of the arms being attached to a slider mechanism for a corresponding one of the blades of the first blade set.
Figure 6:
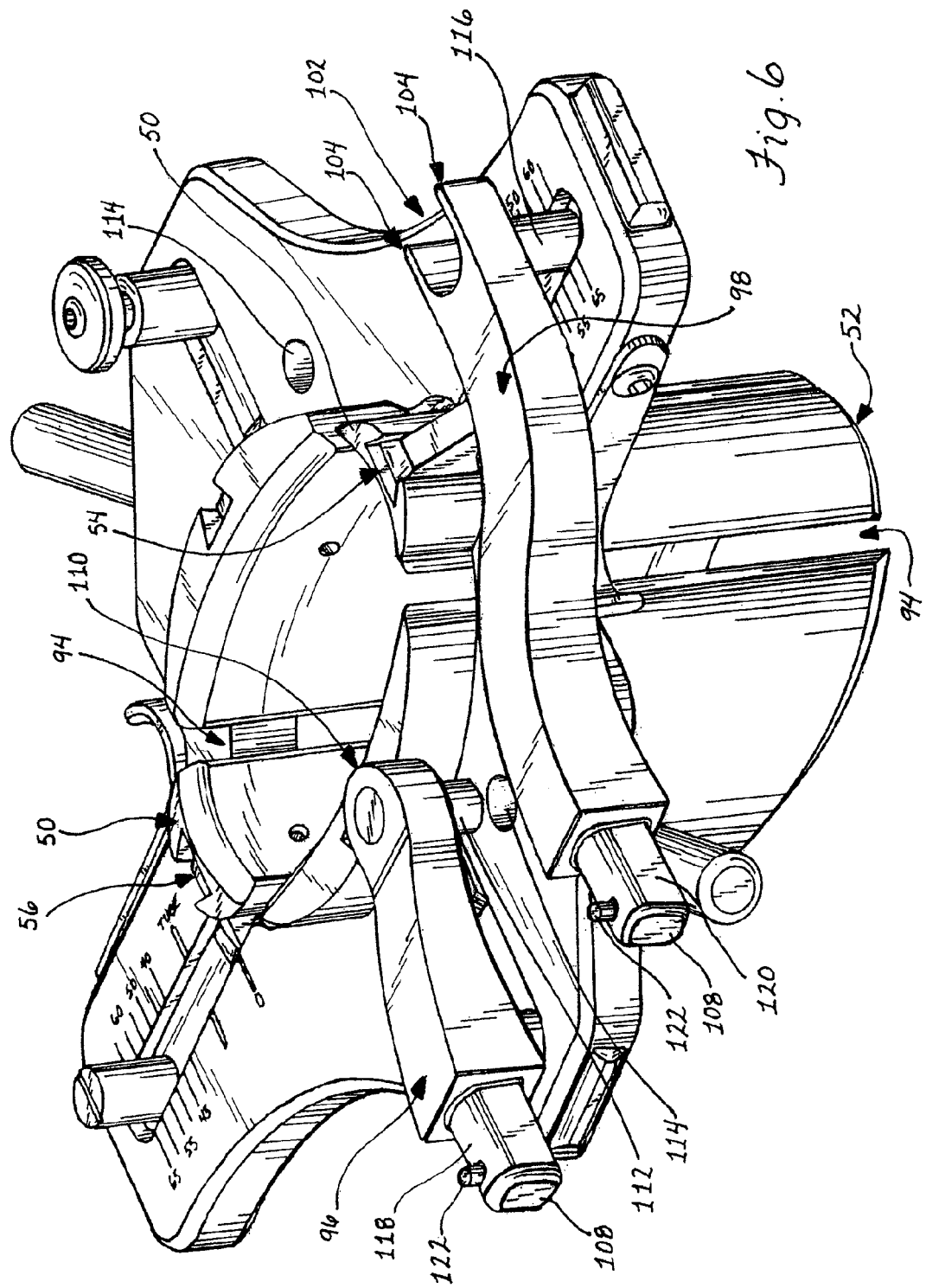
FIG. 6 is a perspective view of the access retractor similar to FIG. 1 and showing the attached connecting arms as in FIG. 5.
Figure 7:
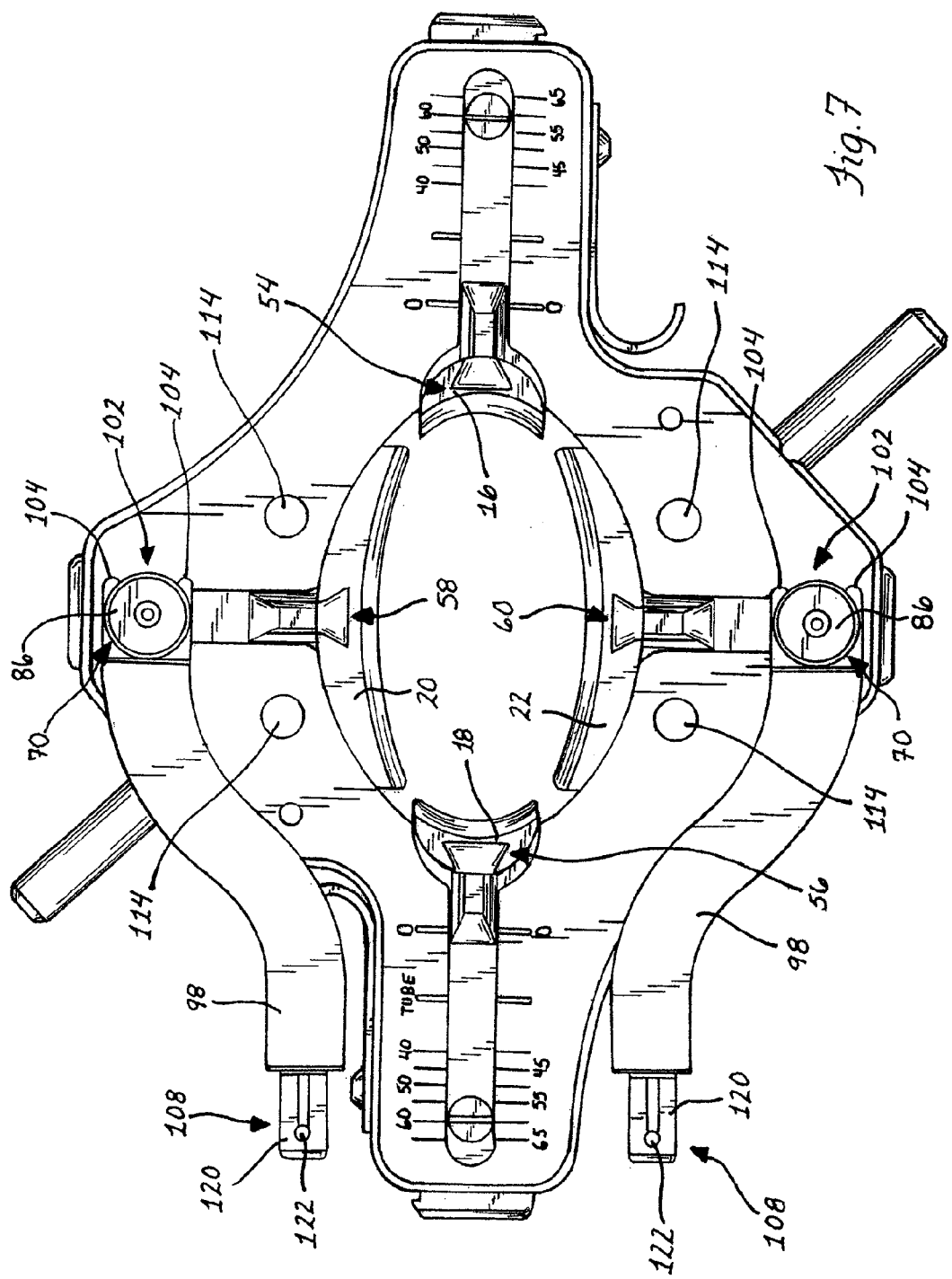
FIG. 7 is a bottom plan view of the access retractor showing the first and second sets of blades in the full retracted positions and another pair of connecting arms attached to the retractor frame with each arm attached to a slider mechanism for opposite blades of the second blade set.

With the blades 20 and 22 inserted into the rectangular incision opening 30 and connected to their sliders 66, 68 as described above, the second stage of the retraction procedure is then undertaken. In this stage, the blades 20 and 22 are retracted in a direction that is transverse to the direction of retraction of the blades 16 and 18 in the initial stage of the retraction procedure. More specifically, the blades 20 and 22 are preferably retracted in a lateral direction 26 that is perpendicular to the longitudinal direction of retraction of the narrow blades 16 and 18 for increasing the size of the incision opening in this direction. This increases the size of the initial rectangular incision opening 30 generated by the narrow blades to a larger width size rectangular opening 92, as shown in FIGS. 5-7. It can be seen that because of the sequential or staggered retraction procedures with the retractor 10 described herein to create the initial or rectangular incision opening 92 allowing for use of the wide blades 20 and 22, spaces or gaps 94 between the adjacent blades 16, 18, 20 and 22 are relatively small once the final size of the incision opening 92 is created after both retraction stages. In this manner, spaces for the encroachment of tissue into the area of the opening that could otherwise obstruct or impede the use of surgical instruments or proper surgical techniques is kept to a minimum. The openings 82 and 84 for receiving the plunger end 80 are also illustrated in FIG. 4.

Each of the sliders 40, 42, 66, and 68 connects to a connection arm 96 or 98 during retraction operations by retraction tool 100. The connecting arm 96 is the shorter arm used during the narrow blade retraction operation. One of the longer connecting arms 98 is used during the narrow blade retraction operations while two long arms 98 are used during the second stage, wide plate retraction procedure. As shown in FIGS. 5 and 6, when either one of the narrow blade slides 40 or 42 is moved, one short connecting arm 96 and one long connecting arm 98 are used so that each of the narrow blades 16 and 18 undergoes retraction independent of the other. However, it is contemplated that both of the narrow blades 16 and 18 can be retracted simultaneously as well. As shown in FIG. 7, when shifting the wide blades 20 and 22 in the second stage, two of the long connecting arms 98 are utilized.

The long connecting arms 98 used to retract the wide blades 20, 22 and slides 66, 68 each generally have an S-shaped configuration and are a mirror image of each other, as can be seen in FIG. 7. The arms 98 have a yoke-shaped end 102 including spaced apart prongs 104 that can be fit about the plunger assembly 70 below the disc handle 86 thereof. At the other end 108, the connecting arms 96 and 98 attach to the spreading instrument or tool 100 that shifts the blades and sliders.

FIGS. 5 and 6 illustrate the connecting arms 96 and 98 attached to the retractor 10 to move the narrow blades 16 and 18 during the initial stage of the retraction procedure. One end 110 of the short connecting arm 96 has a depending peg 112 that mates with an aperture 114 in the frame 12. In addition, the long connecting arm 98 connects to a large slider pin 116 projecting upwardly from the narrow blade sliders 40, 42. This large slider pin 116 is securely gripped by a pair of prongs 104 at the yoke end 102 of the arm 98.

FIG. 7 illustrates the wider blades 20 and 22 having been shifted to the retracted position with two of the long connecting arms 98 secured to the respective plunger assemblies 70. After the prongs 104 of the connecting arms 98 are placed on either side of the plunger assembly 70, the disc handle 86 is pulled up as force is applied to the spreading instrument 100, as described hereinafter, which allows the sliders 66, 68 to be shifted to the retracted position.

As illustrated in FIGS. 6 and 7, opposite the ends 102 and 110 of the connecting arms 96 and 98 are reduced ends 118 and 120 having a generally square configuration with rounded edges and corners that rigidly connect to the spreading instrument 100. The square ends 118 and 120 are each provided with a small spring loaded detent projection to connect the spreading instrument 100 and the connecting arms 96, 98.

Figure 8:
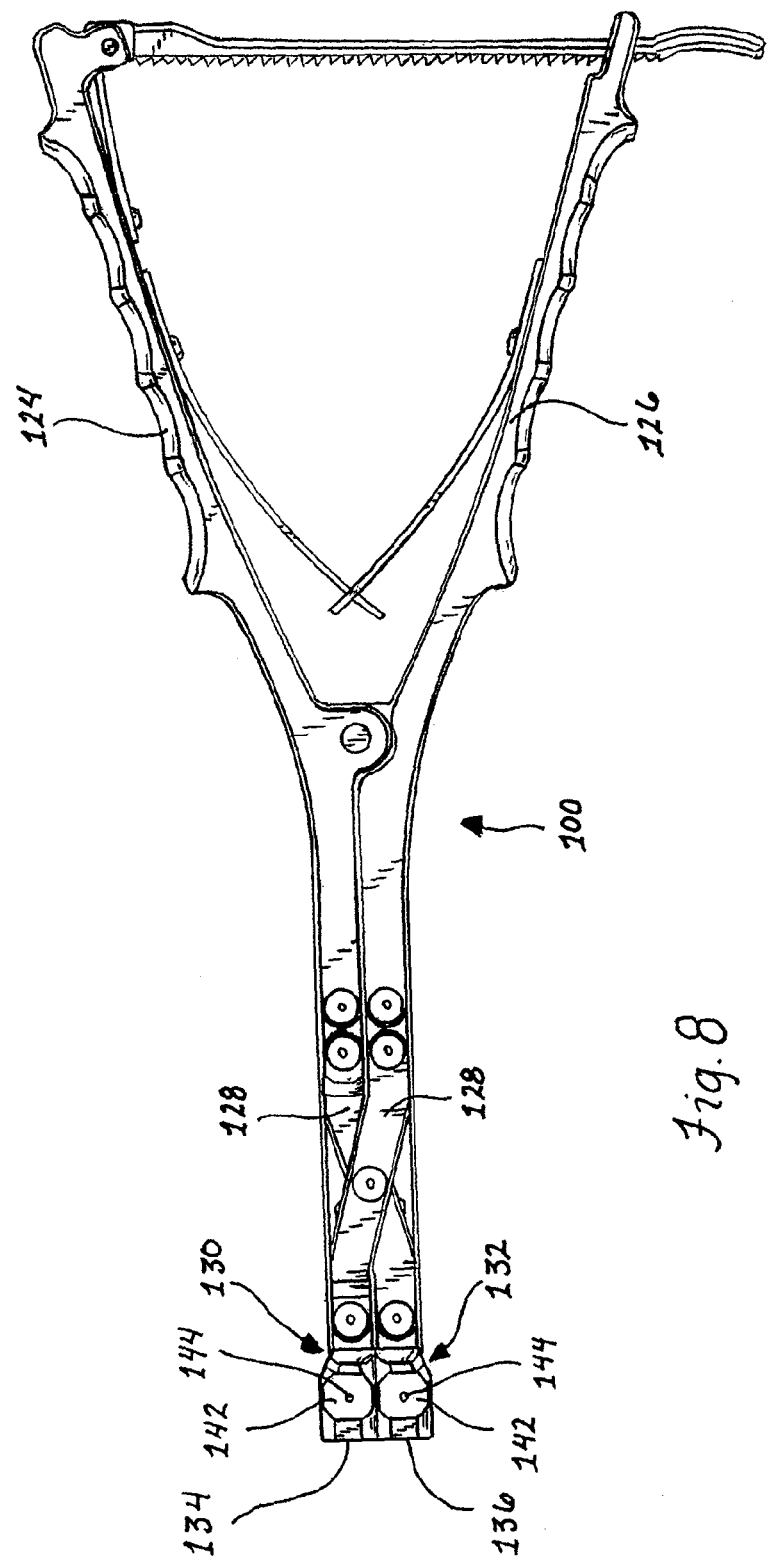
FIG. 8 is a side elevational view of a spreading instrument showing a scissor-arm arrangement including a pair of pivotal operating arms and linkages for actuator arms that are to be attached to the connecting arms.
Figure 9:
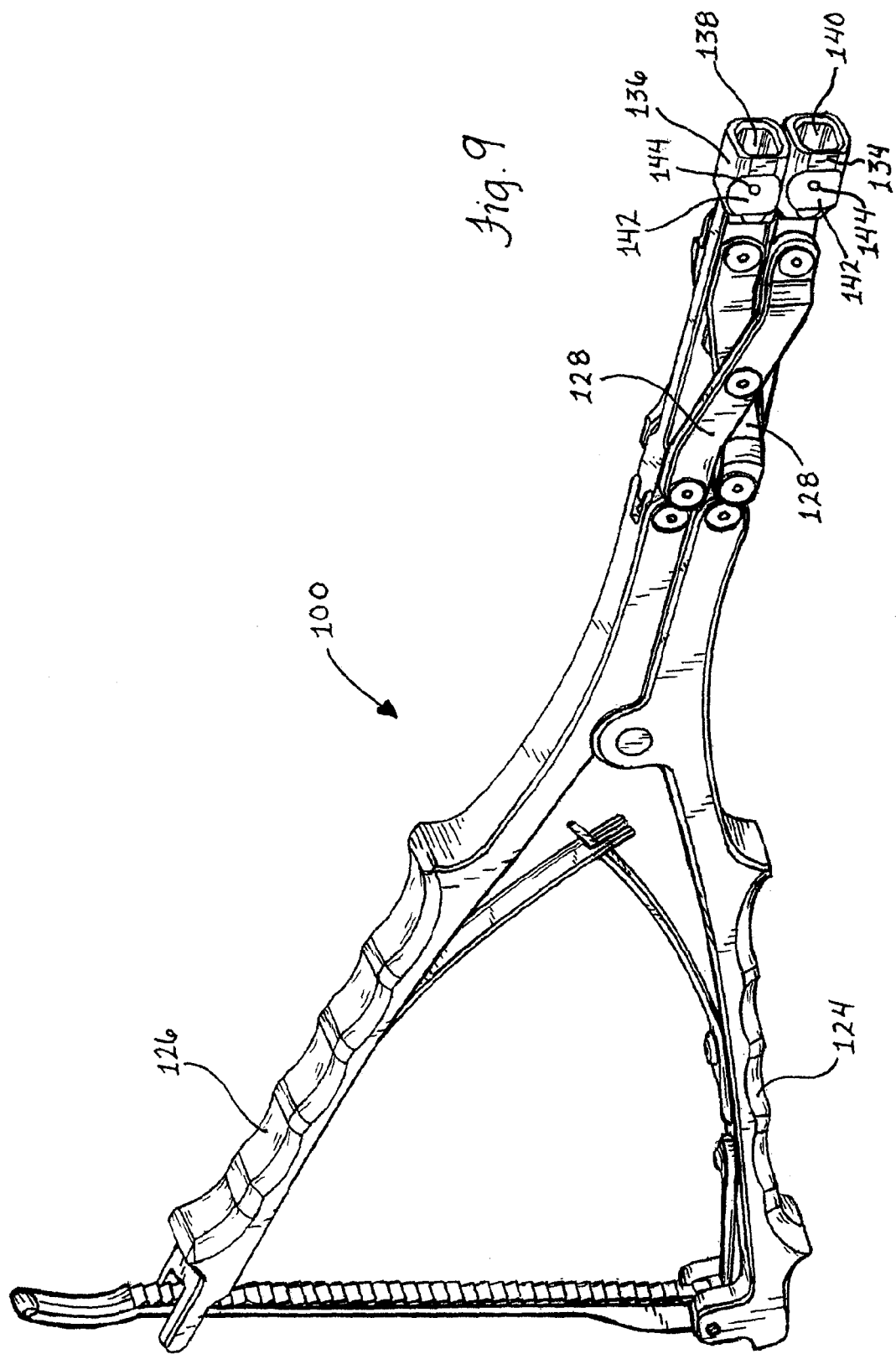
FIG. 9 is a perspective view of the spreading instrument showing a spring loaded ratchet mechanism for the operating arms.
Figure 10:
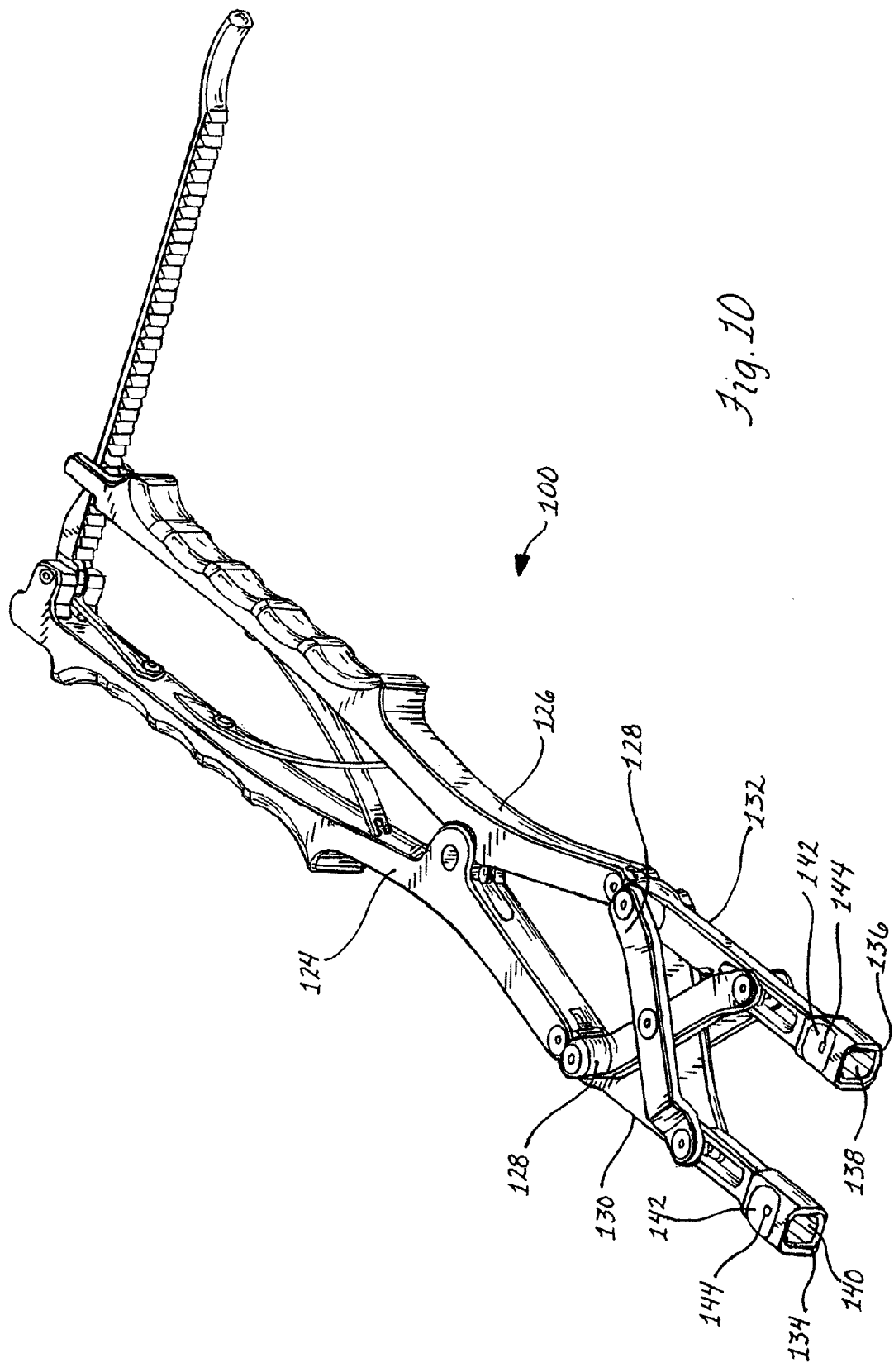
FIG. 10 is a perspective view of the spreading instrument showing the operating arms moved toward each other with the linkages being operable to shift the actuator arms away from each other.
Figure 11:
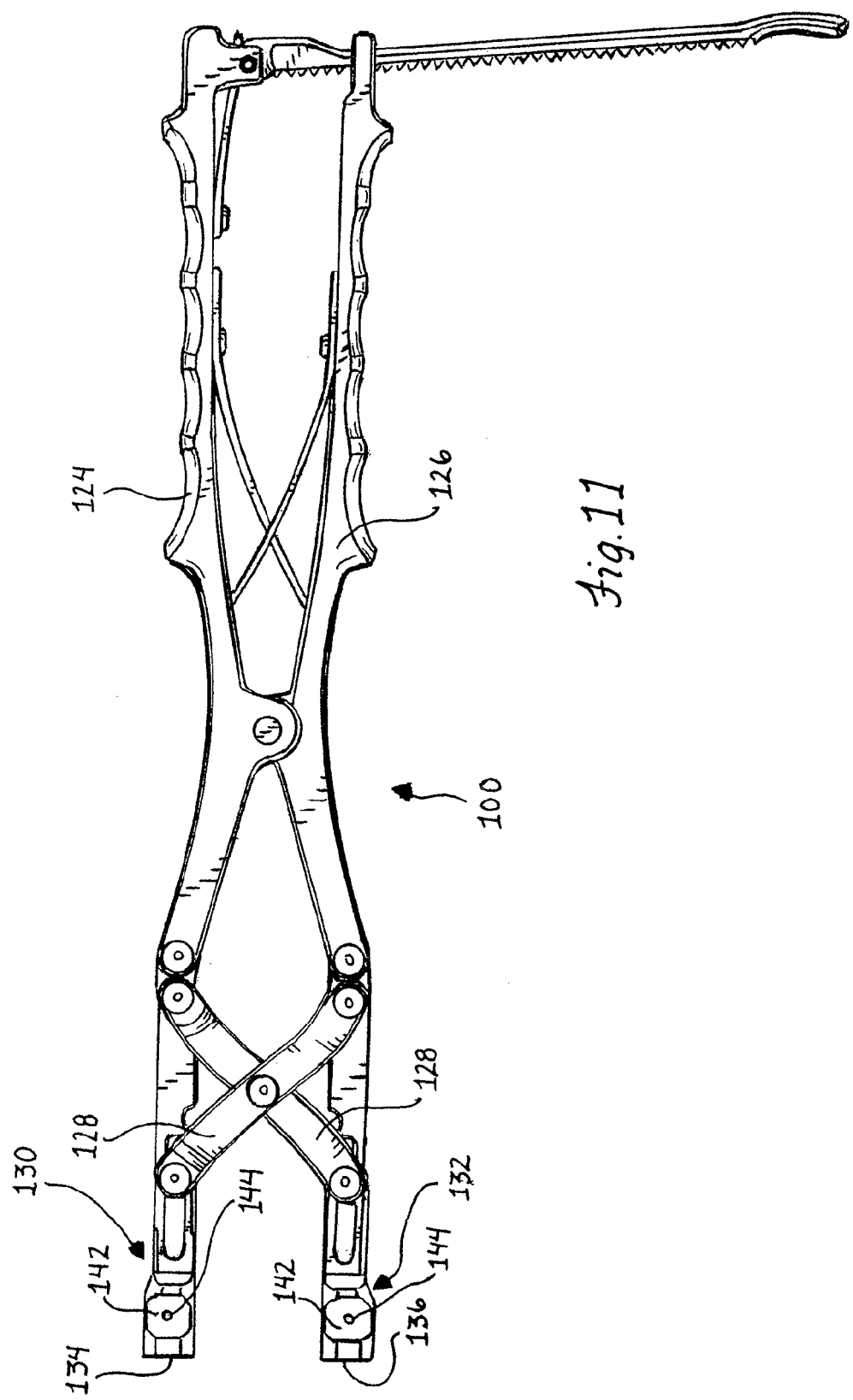

FIGS. 8 and 9 illustrate the spreading tool 100 that attaches to the connecting arms 96 and 98 during the retraction operations. The spreading tool has a pair of pivotal operating arms or handles 124 and 126. When the handles 124, 126 are squeezed, toward each other a corresponding pair of actuator arms move apart from each other staying in parallel orientation via pivotal and slide bar linkages 128 interconnecting the handle arms 124, 126 and actuator arms 130, 132. FIGS. 10 and 11 show the spreading instrument 100 after the spreading operation. Free ends 134 and 136 of the actuator arms 130, 132 have small, open-ended receiving ports 138, 140 including an arcuate cam surface 142 leading to an aperture 144. Inserting the ends 118 and 120 of the connecting arms 96, 98 into the ports 138, 140 causes the detent projection 122 to be depressed against the cam surface 142 until it remedies alignment with the aperture 144. At this point, the projection 122 swaps into the aperture 144 so that the connecting arms 96, 98 are releasably and rigidly connected to spreading tool actuator arms 130, 132.

During the narrow blade 16, 18 retraction procedure, the shorter connecting arm 96 is mounted to the frame 12 by the peg 112 and hole 114. The arm 96 undergoes no movement with respect to the frame 12. Accordingly, squeezing the handles of the tool together only causes the long connecting arm 98 attached to the slider pin 116 to shift relative to the retractor frame which, in turn, causes the connected one of the narrow blade sliders 40, 42, to shift in the longitudinal retraction direction. During the wide blade retraction operation, which uses two longer connecting arms 98, both of the connecting arms undergo movement with respect to the frame 12.

Figure 13:
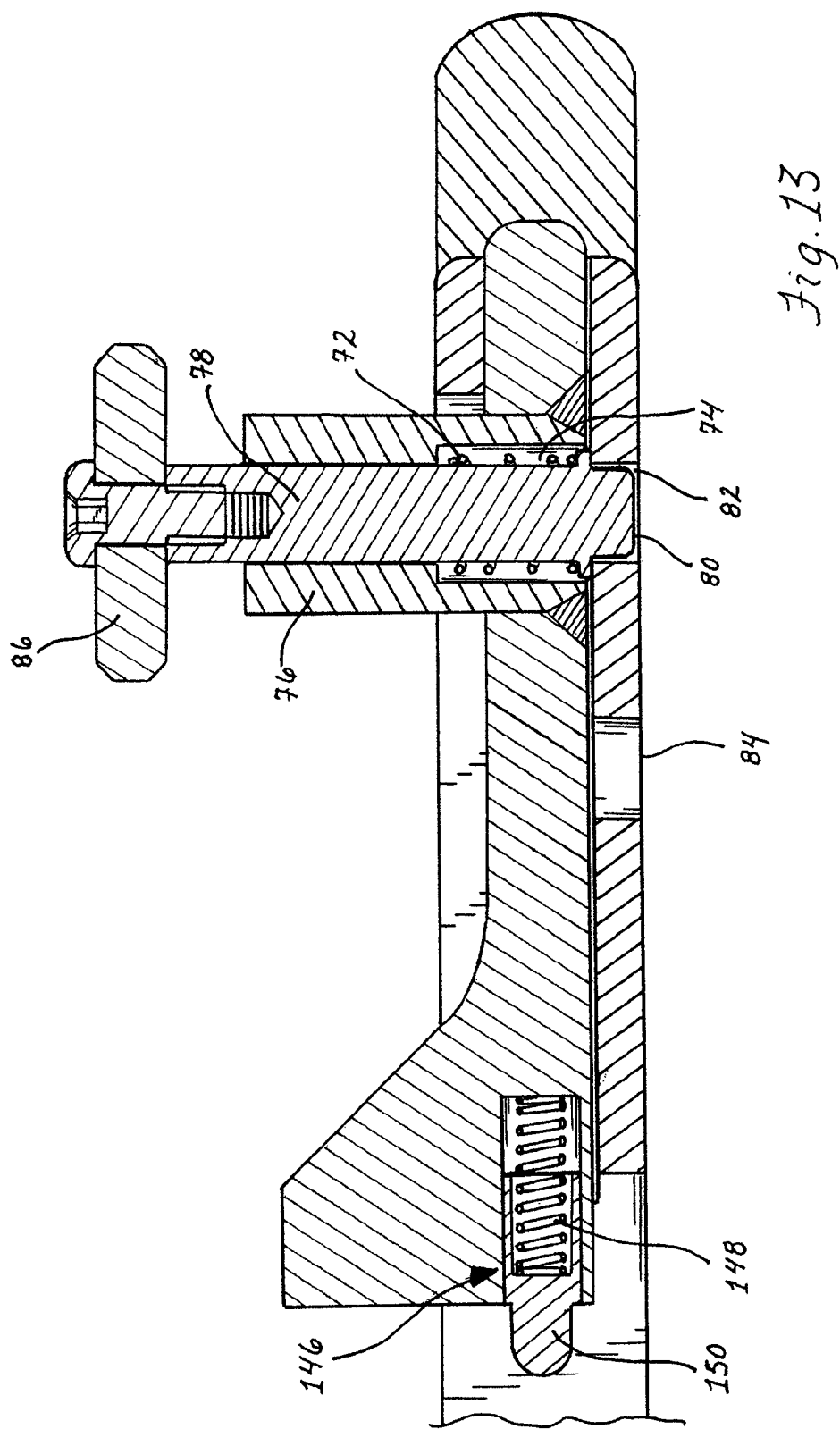
FIG. 13 is a cross-sectional view taken along line 13-13 of FIG. 5 showing a slider mechanism for blades of the second blade set including a slider carrying a detent for forming the detachable connection with the blade and a position selector for releasably fixing the blade in different positions.

After the second retraction operation, the sliders to which the instrument 100 has been attached self-lock into position so that the instrument 100 can be removed form the access retractor 10 without causing the retractor sliders or blades to move. The slider 66, 68, shown in FIG. 13, is depicted locked in the retracted position.

Figure 12:
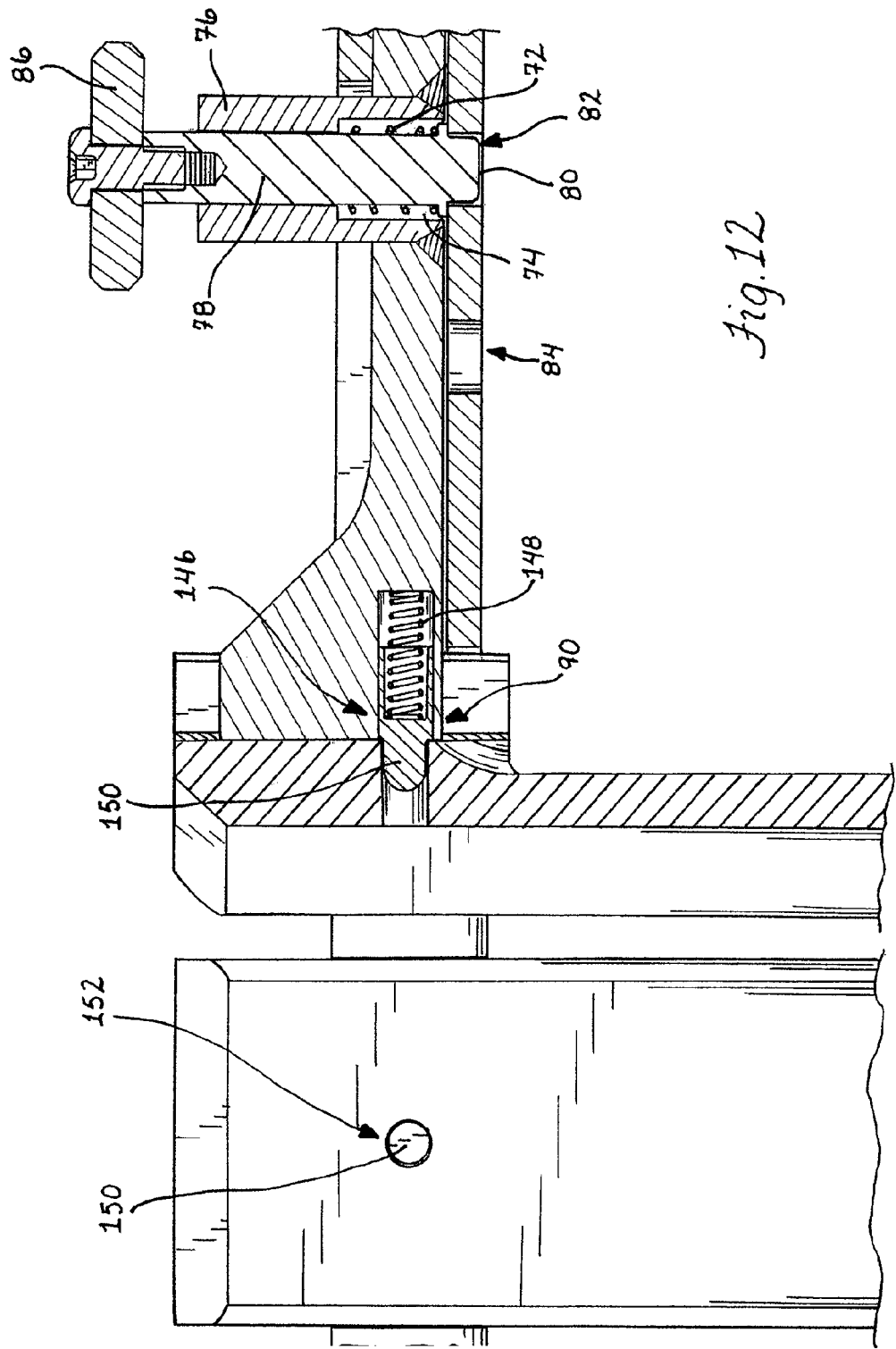
FIG. 12 is a cross-sectional view of the slider mechanism of FIG. 5 with the blade removed.

A spring plunger mechanism 146 located at the end of the sliders 40, 42, 66, 68 prevents unintentional back-out of the blades 16, 18, 20, and 22. The mechanism 146 includes a coil spring 148 attached to a locking pin 150. The pin 150 is biased outward toward the blade 16, 18, 20, and 22. The plunger 146 locks the blades into position on the dovetail joints by pushing the locking pin 150 into the blade aperture 152. FIG. 13 shows the spring plunger mechanism 146 without a blade attached, while FIG. 12 illustrates the wide blade 20, 22 attached to the slider 66, 68. To remove the blades from the dovetail joints 58, 60, an unlocking instrument (not shown) is pushed into a blade aperture 152, as seen in FIG. 1. This disengages the spring plunger mechanism 146 and allows the blades to be removed from the sliders.

Figure 14:
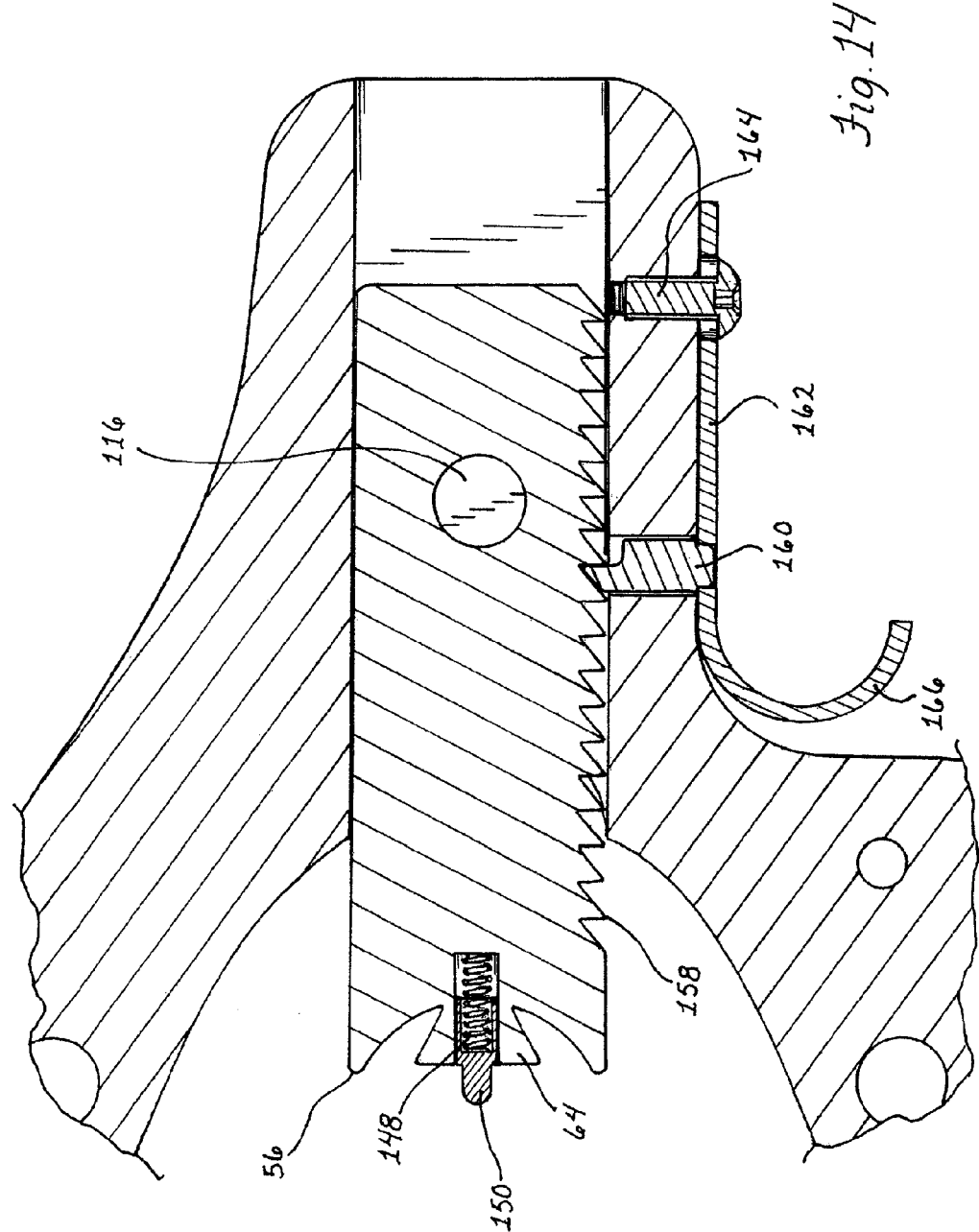
FIG. 14 is a cross-sectional view taken along line 14-14 of FIG. 3 showing a ratchet slider mechanism for blades of the first blade set including a slider carrying a detent for forming the detachable connection with the blade and a position selector for releasably fixing the blade in different positions.
Figure 15:
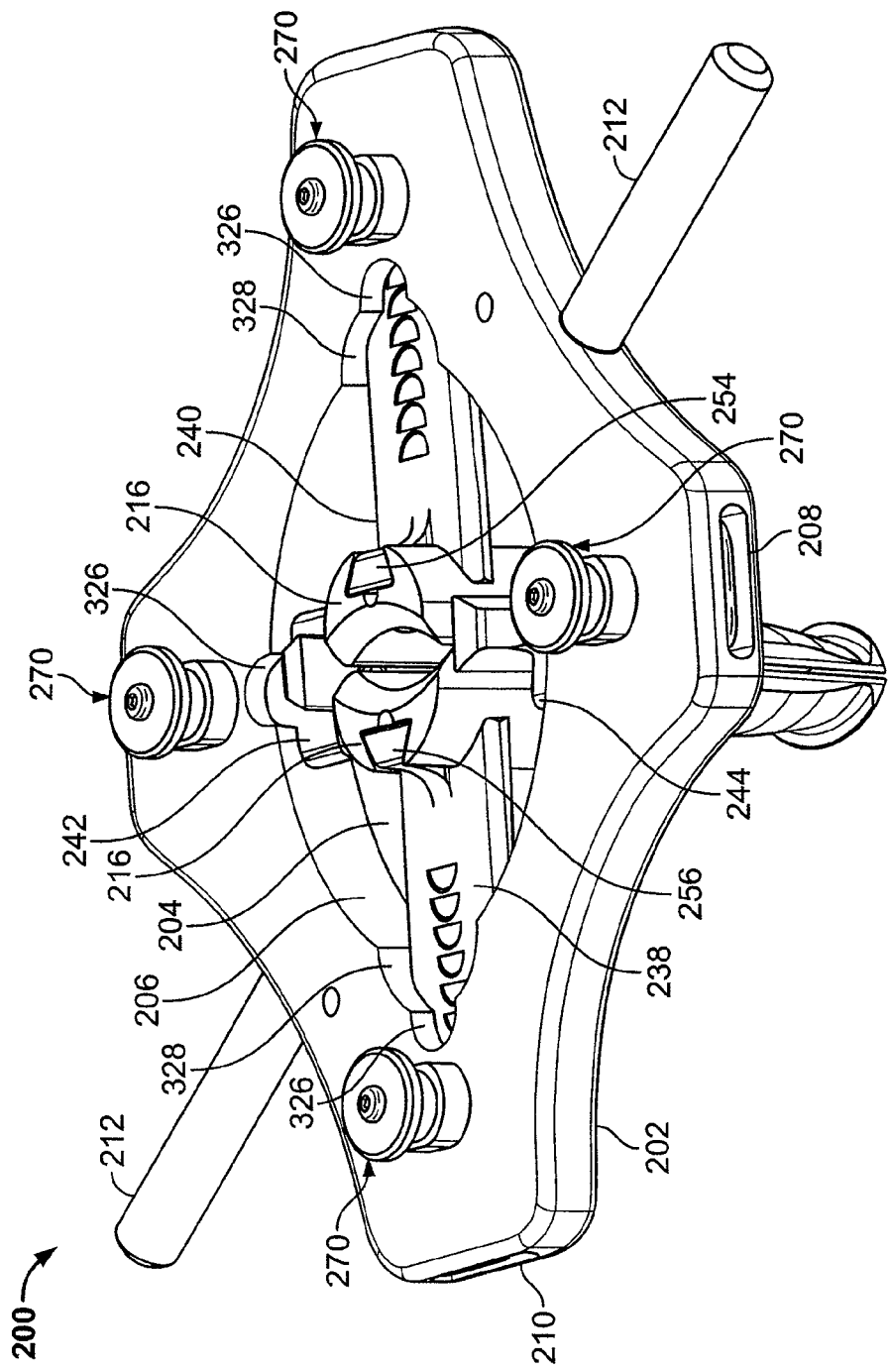
FIG. 15 is a top perspective view of a second embodiment of an access retractor in accordance with the present invention shown with the first set of blades attached to the slider mechanisms of the major axis in an extended position and the slider mechanisms of the minor axis in an intermediate position.
Figure 16:
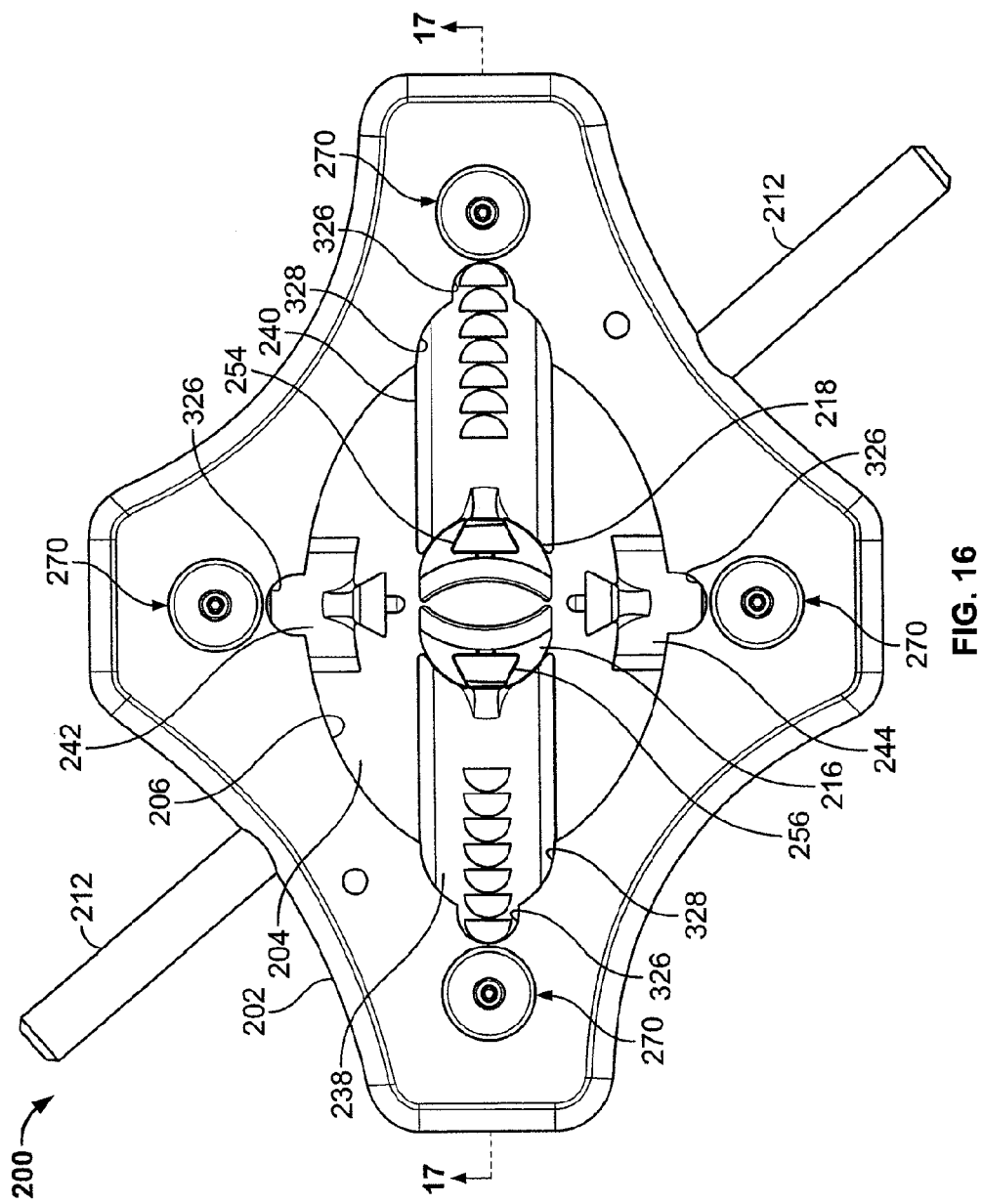
FIG. 16 is a top plan view of the access retractor of FIG. 15.

The spring plungers mechanism 146 is shown in FIG. 14 at the end of the slider 40, 42. As previously discussed, the spring plunger mechanism 146 secures the blades 16, 18 to the sliders 40, 42. FIG. 14 also illustrates the ratcheting mechanism 156 of narrow blade slides 40, 42. The ratcheting slider 40, 42 has teeth 158 that cooperates with a pawl mechanism 160. The pawl mechanism 160 is attached to a leaf spring 162 that is attached to the frame 12 by a screw 164. The pawl 160 is pushed toward the teeth 158 by the leaf spring 162. The ratcheting slider 40, 42 can be moved to the retracted position freely, but to move the narrow blades 16, 18 to the unretracted position, a hook 166 of the leaf spring 162 must be pulled to disengage the pawl 160 from the ratcheting teeth 158.

To steady the access retractor during use, the frame 12 is provided with mounting members 168. The members 168 are located opposite one another on the outside of the frame. These members 168 can be used to attach the retractor 10 to the patient's bed during the surgical procedure such as by using "an iron intern", an example of which is discussed in U.S. Pat. No. 6,302,843, the disclosure of which is hereby incorporated by reference in its entirety.

Figure 19:
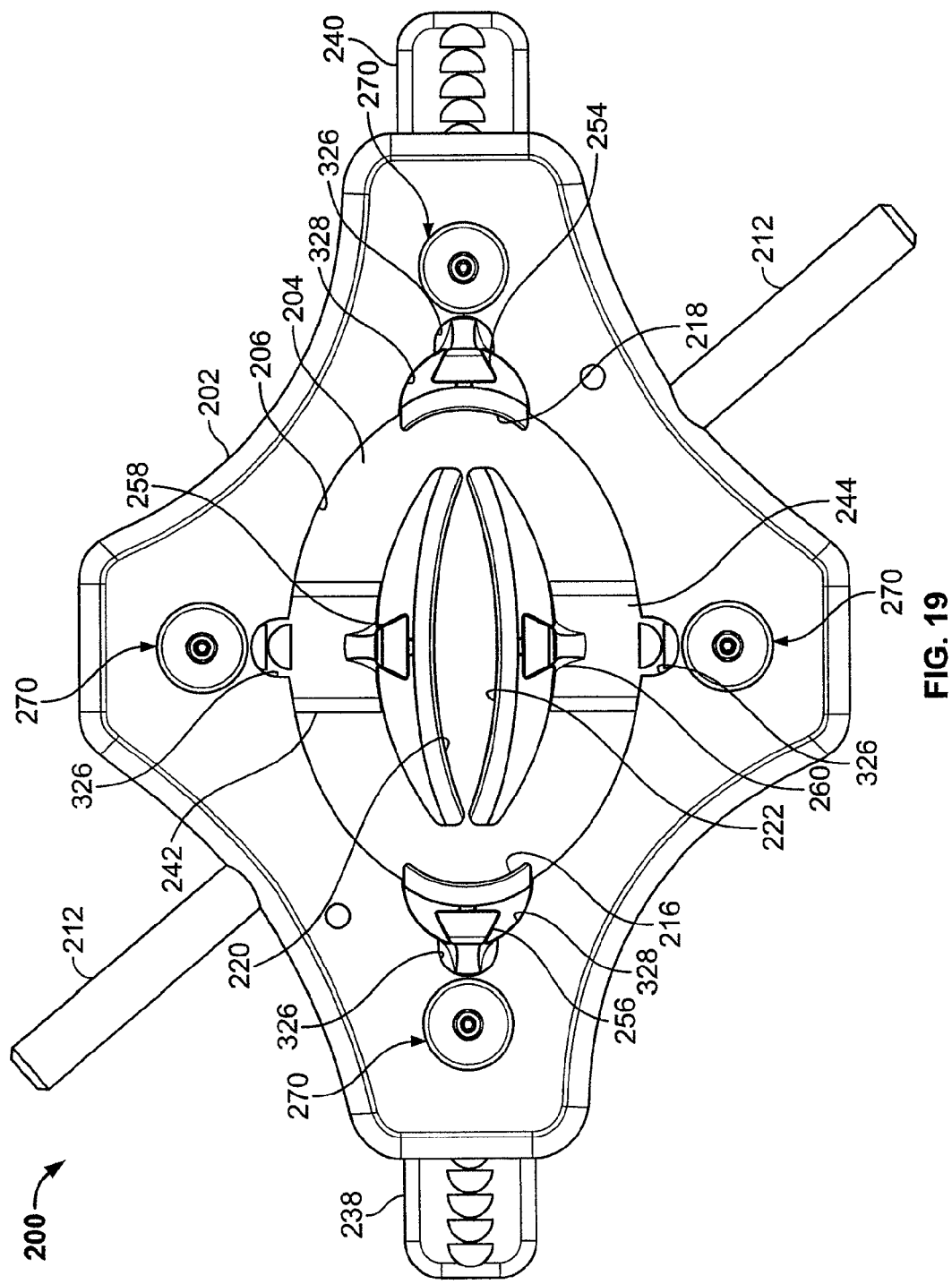
FIG. 19 is a top plan view of the access retractor of FIG. 15 with the slider mechanisms associated with the first set of blades in a fully retracted position and the second set of blades attached to the slider mechanisms of the minor axis in an extended position.
Figure 20:
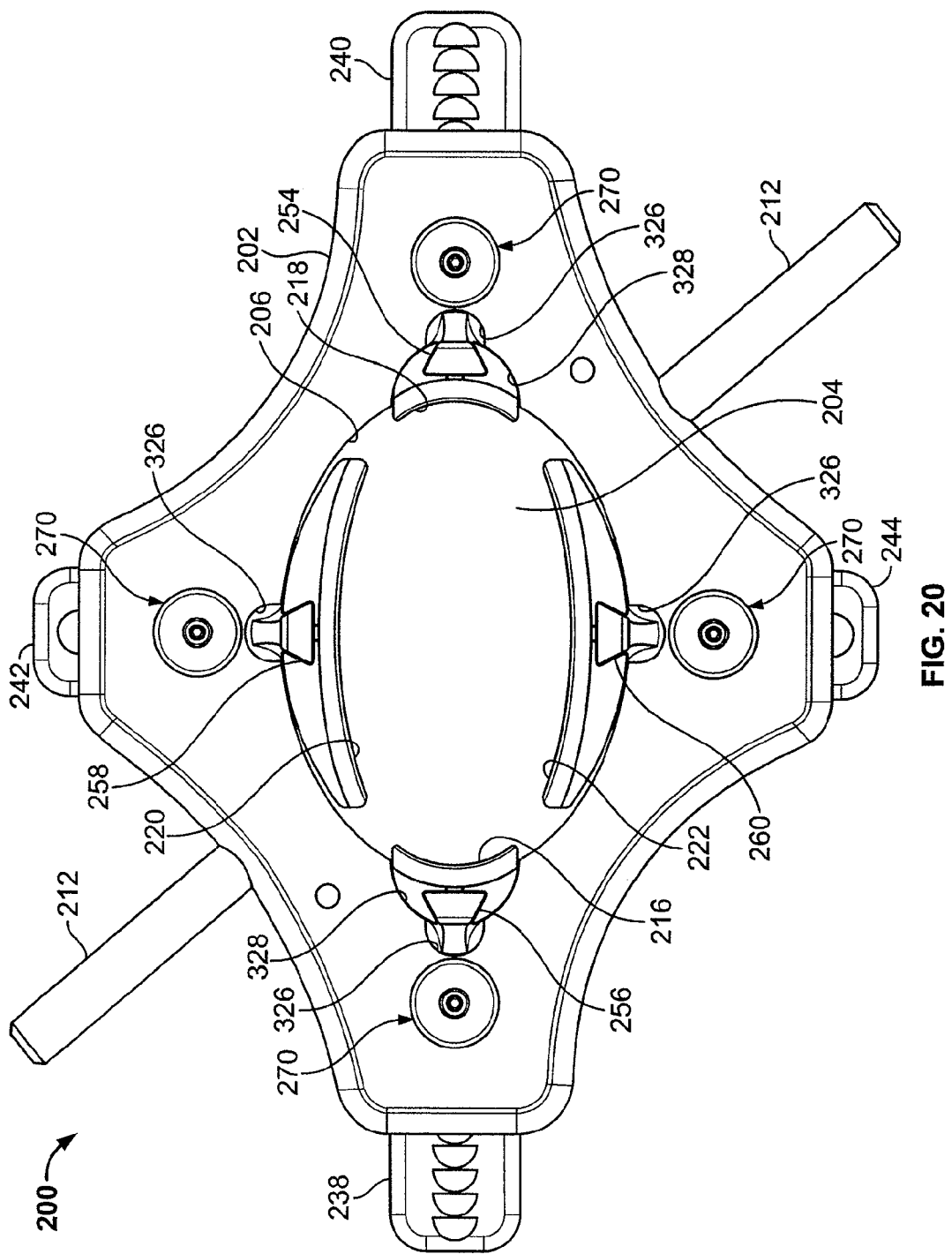
FIG. 20 is a top plan view of the access retractor of FIG. 15 with the slider mechanisms associated with the first set of blades in a fully retracted position and the slider mechanisms associated with the second set of blades in a fully retracted position.
Figure 21:
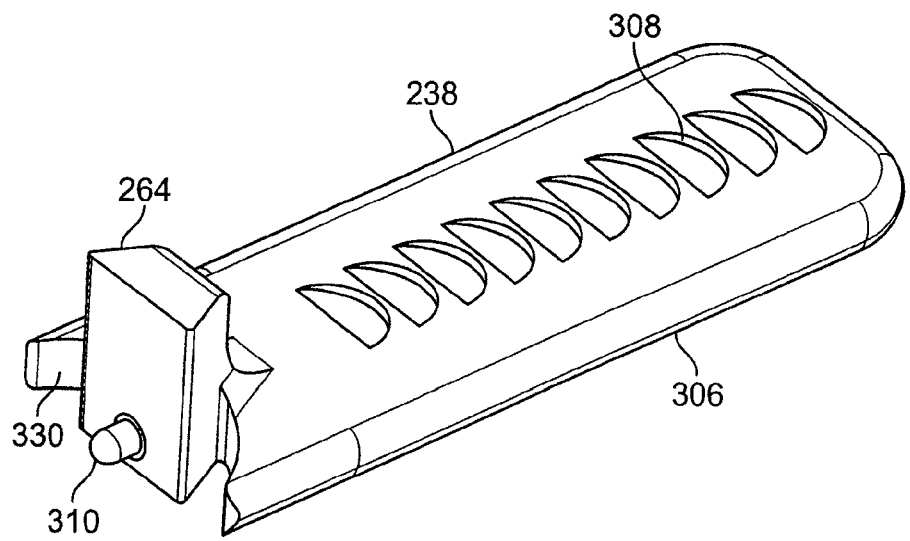
FIG. 21 is a perspective view of a slider mechanism of FIG. 15 for use with the first set of blades.
Figure 22:
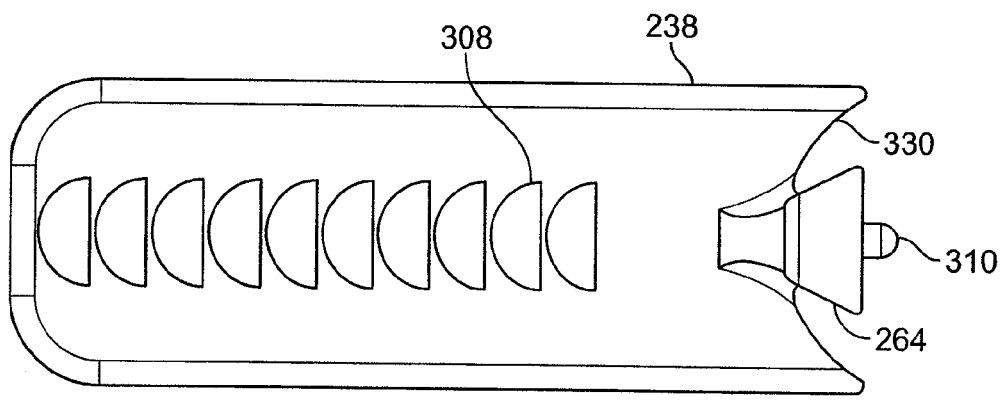
FIG. 22 is a top plan view of the slider mechanism of FIG. 21.
Figure 23:
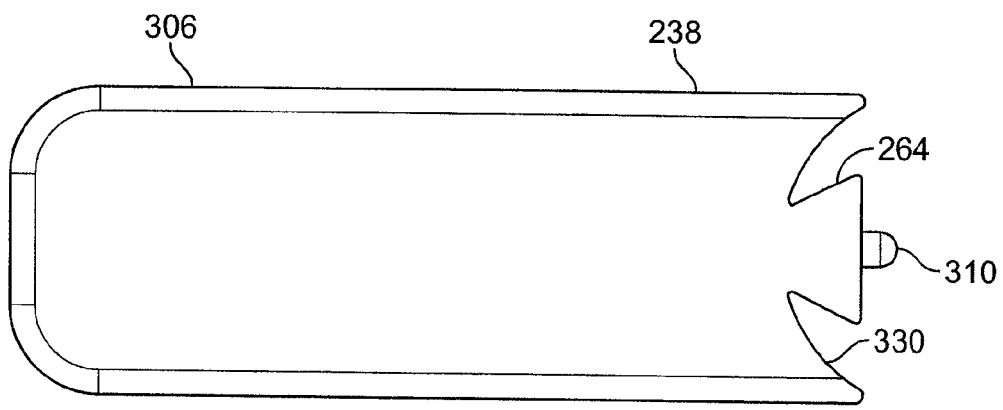
FIG. 23 is a bottom plan view of the slider mechanism of FIG. 21.
Figure 24:
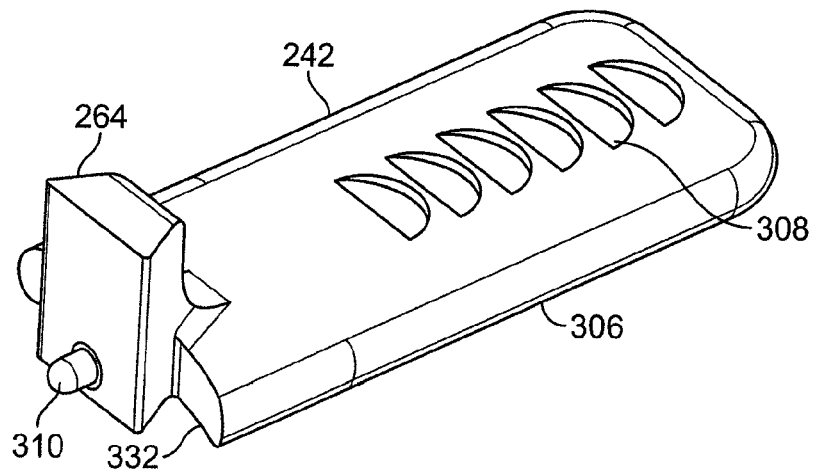
FIG. 24 is a perspective view of a slider mechanism of FIG. 15 for use with the second set of blades.
Figure 25:
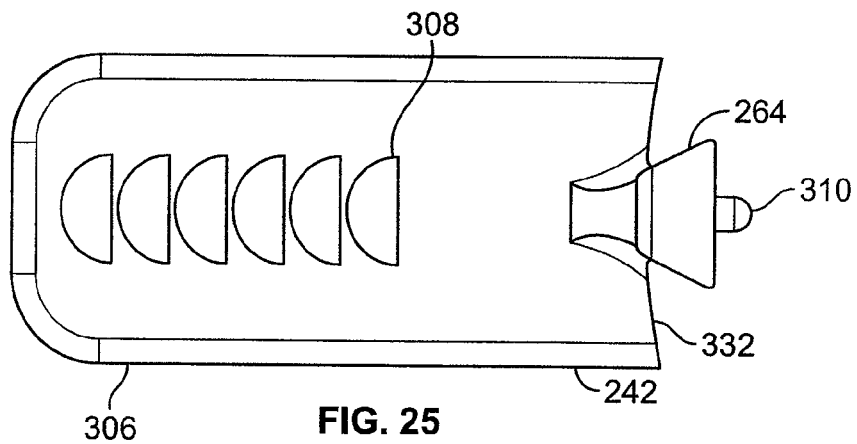
FIG. 25 is a top plan view of the slider mechanism of FIG. 24.
Figure 26:
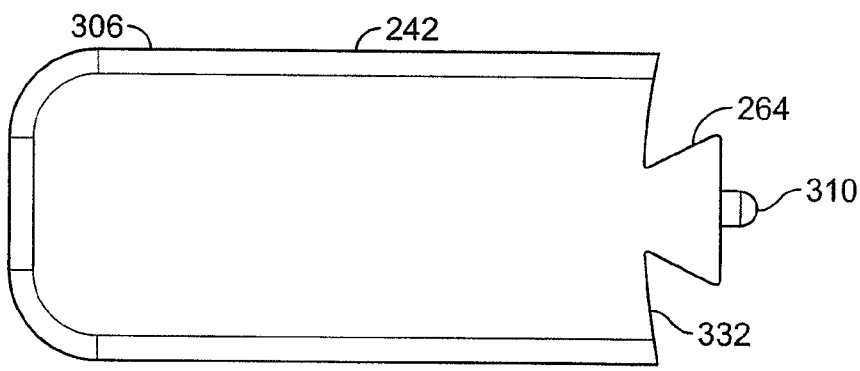
FIG. 26 is a bottom plan view of the slider mechanism of FIG. 24.

Turning now to a second embodiment, the access retractor 200 of FIGS. 15-32 is similar to the access retractor 10 of FIGS. 1-7 and 12-14, in that it comprises a generally planar body or frame 202 having a central, oblong or ovular opening 204. Opposing sliders 238, 240 and 242, 244 that slide in through slots 208 and 210 formed in both a longitudinal direction and a transverse direction. A first set of tissue engaging members, in this example comprising narrow blades 216 and 218, are releasably connected to associated sliders 238 and 240, as illustrated in FIG. 15-17, 19 and 20. A second set of tissue engaging members, in this example comprising wide blades 220 and 222, are releasably connected to associated sliders 242 and 244, as illustrated in FIGS. 19 and 20.

One difference between the first embodiment of the access retractor 10 and the second embodiment of the access retractor 200 is that the latter uses a ratchet mechanism associated with each of the sliders 238, 240, 242 and 244 in order to permit movement of the sliders 238, 240, 242 and 244 toward their retracted positions while restricting movement toward their extended positions. Another difference between the first embodiment of the access retractor 10 and the second embodiment of the access retractor 200 is that the latter can be used with a spreading instrument in direct contact with the blades 216, 218, 220 and 222 in order to manipulate the sliders 238, 240, 242 and 244 (and attached blades 216, 218, 220 and 222) between their extended and retracted positions relative to the opening 204 of the frame 202. These differences, and others, will be discussed in greater detail herein.

The frame 202 of the second embodiment of the access retractor 200 is similar in shape to the frame or body 12 of the first embodiment of the access retractor 10, being generally planer and having a centrally disposed, oblong or ovular retention opening 204 surrounded by an inner wall 206. Also similar to the access retractor 10 of the first embodiment, the frame 202 of the access retractor 200 of the second embodiment includes two pairs of opposing through slots 208 and 210, including a pair of transverse through slots 208 and a pair of opposing longitudinal through slots 210. The transverse through slots 208 are aligned with the transverse or minor axis of the frame 202, and the longitudinal through slots 210 are aligned with the longitudinal or major axis of the frame 202.

A pair of opposing rods 212 extend from the frame 202 to permit attachment of the access retractor 200 relative to a stationary frame or table using intermediate arms, such as the "iron intern."

Sliders 238, 240, 242 and 244 are positioned in the slots 208 and 210 of the frame 202. The sliders 238, 240, 242 and 244 each have a dovetail connection 254, 256, 258 and 260, respectively, to an associated blade 216, 218, 220 and 222. The dovetail connections 254, 256, 258 and 260 are configured to both permit releasable attachment of the blades 216, 218, 220 and 222 to an associated one of the sliders 238, 240, 242 and 244 and to position the attached blades 216, 218, 220 and 222 in the opening 204 of the frame 202, as in the first embodiment. A releasable connection or locking mechanism 310, similar to the releasable connection 90 discussed above, is provided for each slider 238, 240, 242 and 244 to permit locking of an associated one of the blades 216, 218, 220 and 222, and will be discussed in greater detail below.

As with the first embodiment, the releasable dovetail connections 254, 256, 258 and 260 and releasable connections 310 permit pairs of the blades 216, 218 and 220, 222 to be attached to the associated sliders 238, 240 and 242, 244 in a sequential manner to enable multi-stage stretching of the incision while minimizing gaps between adjacent ones of the blades 216, 218, 220 and 222 when each are in a retracted stage to reduce the encroachment of retracted tissue surrounding the incision between adjacent ones of the blades 216, 218, 220 and 222 and into the surgical site during surgical procedures. More specifically, the narrow blades 216 and 218 can be inserted into an incision, and in particular an incision that has been dilated to a size sufficient to accommodate the width of the narrow blades 216 and 218, and then attached to the associated sliders 238 and 240 using the dovetail connections 254 and 256 and releasable connections 310 to secure the blades 216 and 218 in an extended or initial stage. The sliders 238 and 240 can then be retracted to use the attached narrow blades 216 and 218 to enlarge the incision to an intermediate stage. Once the incision is enlarged in the intermediate stage, the wide blades 220 and 222 can be inserted into the enlarged opening and attached to the associated sliders 242 and 244 in their extended positions. Finally, the sliders 242 and 244 can be moved toward their retracted positions to use the attached wide blades 220 and 222 to further enlarge the incision in a final stage. The result, as in the first embodiment, is an oblong-shaped opening bounded by closely adjacent blades 216, 218, 220 and 222.

Figure 33:
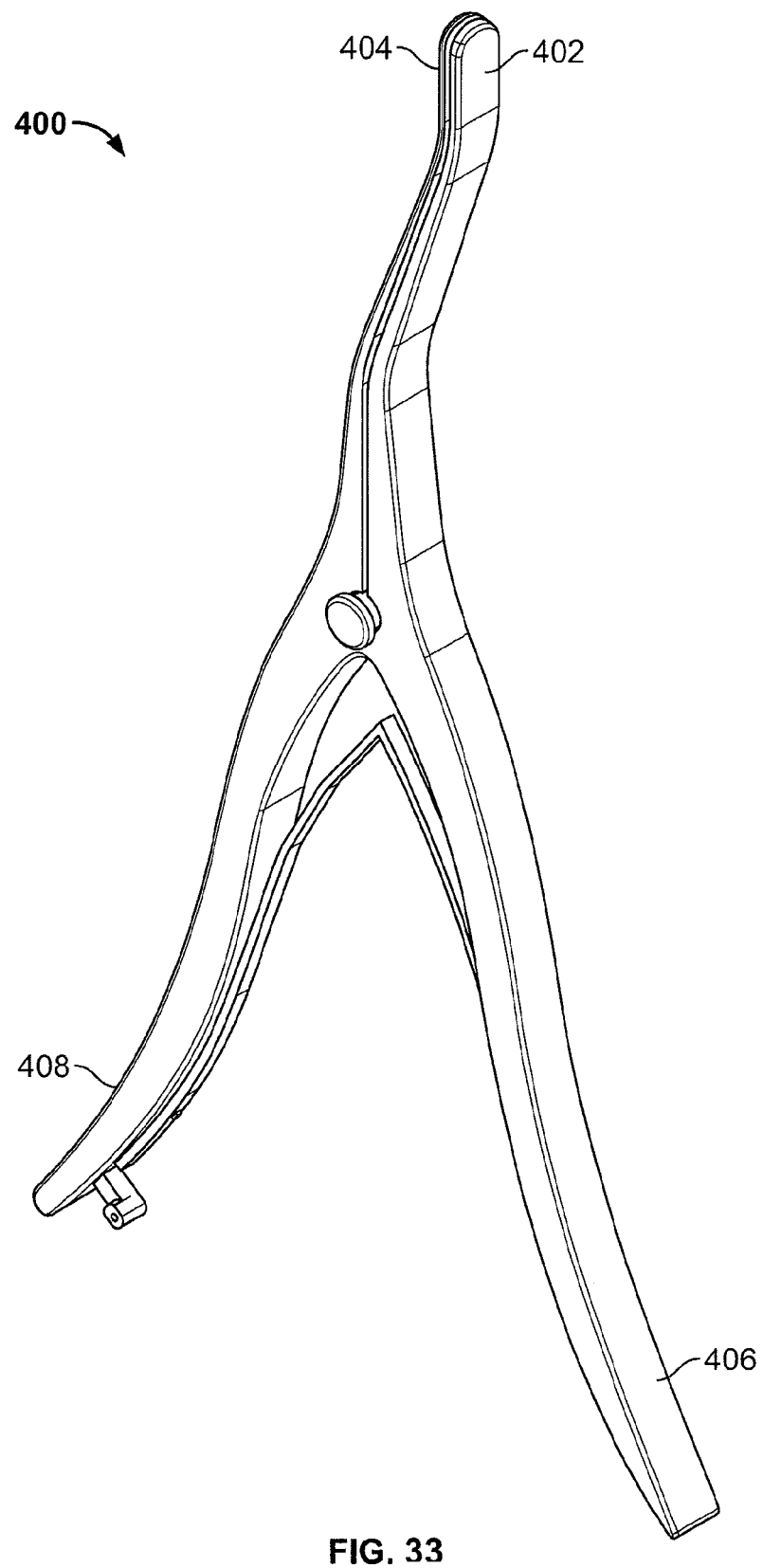
FIG. 33 is a perspective view of a spreading instrument that can be used to retract opposing blades.

Also as in the first embodiment, a spreading instrument may be used to provide a mechanical advantage to assist in moving the blades 216, 218, 220 and 222 toward their retracted positions and thereby stretch the incision. Although the retraction tool 100 and connection arms 96 and 98 can be used, as in the first embodiment, a lamina spreader 400, such as illustrated in FIG. 33, can be used instead. To use the lamina spreader, each operating end 402 and 404 of the lamina spreader 400 can be placed in abutment with the inward facing surfaces of an opposing pair of blades 216, 218 and 220, 222. The handles 406 and 408 of the lamina spreader 400 can then be manipulated to force the abutted opposing pair of blades 216, 218 and 220, 222 in opposing directions and toward their retracted positions. Ratchet mechanisms associated with each of the sliders 238, 240, 242 and 244 permit incremental retraction of the attached blades 216, 218, 220 and 222 while resisting the pulling force of the surrounding tissue to urge the blades 216, 218, 220 and 222 back toward their extended positions. The lamina spreader 400 may be of the type sold by Life Instrument Corporation, Braintree, Mass., as model number 741-1106-1, with the modifications being disablement of the ratchet mechanism and removal of the teeth on the operating ends 402 and 404.

The sliders 238, 240, 242 and 244 are each generally identical in construction, with the exception of their lengths, the number of ratchet teeth 308 and the radius of the arc 330 or 332 on the end disposed in the opening 204, as will be discussed in greater detail below. Each of the sliders 238, 240, 242 and 244 includes, with reference to narrow blade slider 238 of FIGS. 21-23 and the wide blade slider 242 of FIGS. 24-26, a generally flat shank 306 having an upstanding dovetail projection 264 at one end. A plurality of ratchet teeth 308 are disposed along a longitudinal axis of the shank 306 for engagement with a plunger 290 of the plunger assembly 270 to restrict movement of the slider 238 toward the extended position but not toward the retracted position. The dovetail projection 264 is dimensioned to mate with a corresponding dovetail recess 262 formed on each of the blades 216, 218, 220 and 222. In order to provide clearance for the dovetail connections 254, 256, 258 and 260, and in particular the dovetail projections 264, arcuate recesses 326 are formed in the inner wall 206 of the frame 202 and are aligned with the sliders 238, 240, 242 and 244, as illustrated in FIGS. 15-17, 19 and 20. An additional arcuate recess 328 is also provided in the inner wall 206 of the frame 202 for each of the narrow blade sliders 238 and 240 in their retracted positions.

The end of the shank 306 adjacent the dovetail projection 264 includes one of two arcs 330 or 332 facing inward toward the opening 204 of the frame 202. Each of the arcs 330 and 332 has a different radius. In particular, the wide blade sliders 242 and 244 each have the arc 332 with the greater radius, and the narrow blade sliders 238 and 240 each have the arc 330 with the lesser radius. The different radii of the arcs 330 and 332 have two different functions.

First, the arcs 330 and 332 function to ensure that only the wide blades 220 and 222 are attached to the wide blade sliders 242 and 244 and that only the narrow blades 216 and 218 are attached to the narrow blade sliders 238 and 240. More specifically, each of the arcs 330 and 332 has a radius that corresponds to a radius 233 on the narrow blades 216 and 218 and a radius 234 on the wide blades 220 and 222, respectively, in a region adjacent the dovetail recess 262. This is to ensure that only the wide blades 220 and 222 are attached to the wide blade sliders 242 and 244 and that only the narrow blades 216 and 218 are attached to the narrow blade sliders 238 and 240. The difference in the radii of the arc 330 of the narrow blade sliders 238 and 240 and the region adjacent the dovetail recess 262 on the wide blades 220 and 222 prevents the wide blades 220 and 222 from being attached to the narrow blade sliders 238 and 240. Likewise, the difference in the radii of the arc 332 of the wide blade sliders 242 and 244 and the region adjacent the dovetail recess 262 on the narrow blades 216 and 218 prevents the narrow blades 216 and 218 from being attached to the wide blade sliders 242 and 244. In this manner, proper attachment of the respective ones of the narrow blades 216 and 218 and wide blades 220 and 222 with the associated slider 238, 240, 242 and 244 is assured.

Second, the arcs 330 and 332 function to provide a flush surface with adjacent portions of the inner wall 206 of the frame 202 surrounding the opening 204 in order to restrict intrusion of unnecessary components into the opening 204 when the sliders 238, 240, 242 and 244 are fully retracted. The arc 330 having the lesser radius, on the narrow blade sliders 238 and 240, is able to be flush with the adjacent portion of the inner wall 206 of the frame 202 when the sliders 238 and 240 are fully retracted due to a corresponding arcuate surface formed on the adjacent portion of the inner wall 206, as illustrated in FIG. 20. Similarly, the arc 332 having the greater radius, on the wide blade sliders 242 and 244, is able to be flush with the adjacent portion of the inner wall 206 of the frame 202 when the sliders 242 and 244 are fully retracted due to a corresponding arcuate surface formed on the adjacent portion of the inner wall 206, as also illustrated in FIG. 20.

The sliders 238 and 240 extending in the longitudinal direction of the frame 202, and associated with the narrow blades 216 and 218, have lengths greater than the lengths of the sliders 242 and 244 extending in the transverse direction of the frame 202, and associated with the wide blades 220 and 222. The difference in lengths of the narrow blade sliders 238 and 240 compared to the wide blade sliders 242 and 244 is to permit all the blades 216, 218, 220 and 222 to be positionable in a center region of the opening 204 of the frame 202 when the sliders 238, 240, 242 and 244 are in the fully extended positions. To accommodate the different in length of the major axis as compared to the minor axis of the oblong or ovular shaped opening 204 of the frame 202, the narrow blade sliders 238 and 240 are longer than the wide blade sliders 242 and 244. Because the longer narrow blade sliders 238 and 240 have a greater distance of travel to go from the fully extended to fully retracted positions as compared to the shorter wide blade sliders 242 and 244, the narrow blade sliders 238 and 240 have a greater number of ratchet teeth 308 than the wide blade sliders 242 and 244, and thus more discrete positions.

Figure 27:
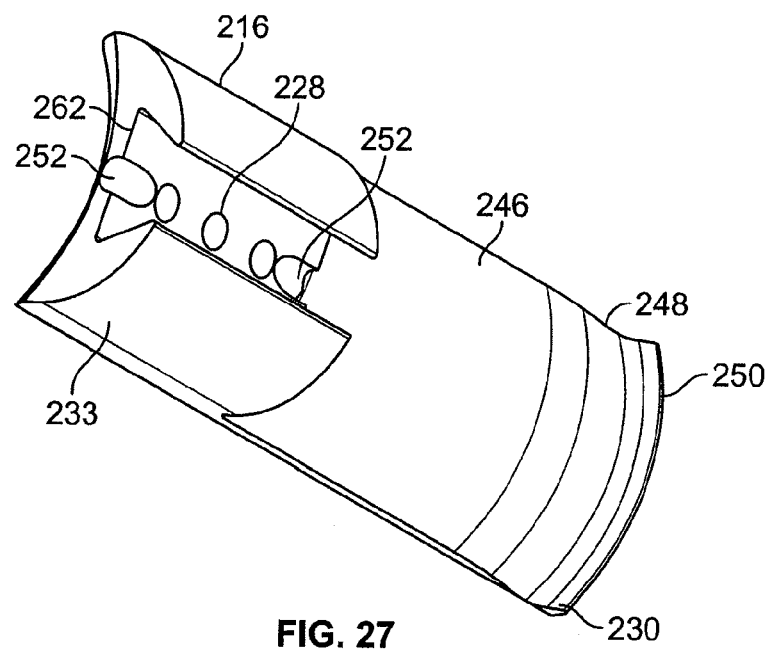
FIG. 27 is a rear perspective view of one of the first set of blades of FIG. 15.
Figures 28, 29:
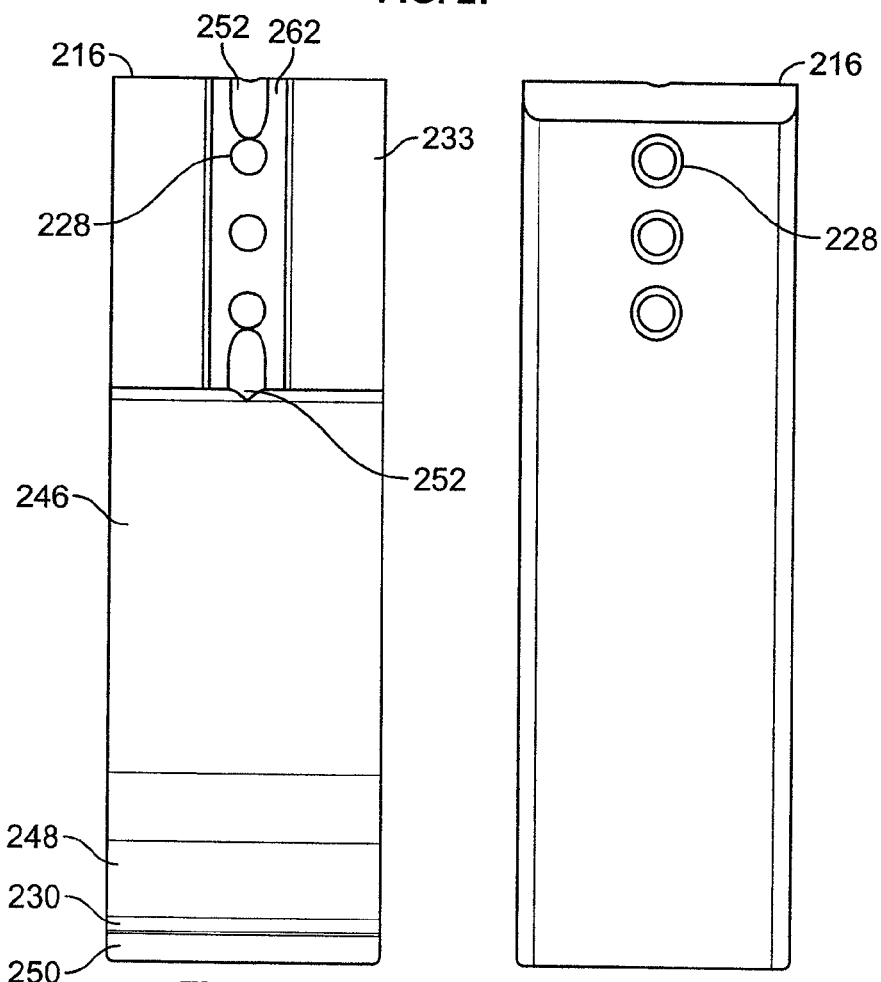
FIG. 28 is a rear elevation view of the blade of FIG. 27.
FIG. 29 is a front elevation view of the blade of FIG. 27.

The blades 216, 218, 220 and 222 are similar in construction to each other, with the primary exceptions of the differences in width between the narrow blades 216, 218, illustrated in FIGS. 27-29, and the wide blades 220, 222, illustrated in FIGS. 30-32, and the different arcs 330 and 332. The upper end of the blades 216, 218, 220 and 222 each include a dovetail recess 262 for mating with the dovetail projection 264 of the associated slider 238, 240, 242 and 244. An opposite end of the blades 216, 218, 220 and 222 includes a lip 230, which in use faces outward from the opening 204 of the frame 202 to assist in maintaining the adjacent tissue from slipping under the blades 216, 218, 220 and 222. The opposite end of the blades 216, 218, 220 and 222 also includes an inclined ramp 250 to facilitate insertion of the blades 216, 218, 220 and 222 into the surgical opening in a manner that urges the tissue outwardly relative to the opening 204 of the frame 202. Positioned immediately adjacent the lip 230 and opposite the inclined ramp 250 is an inwardly inclined surface 248, which in use is configured to direct adjacent tissue surrounding the surgical opening into the crook of the lip 230. The blades 216, 218, 220 and 222 are similar in size to those of the first embodiment.

Figure 17:
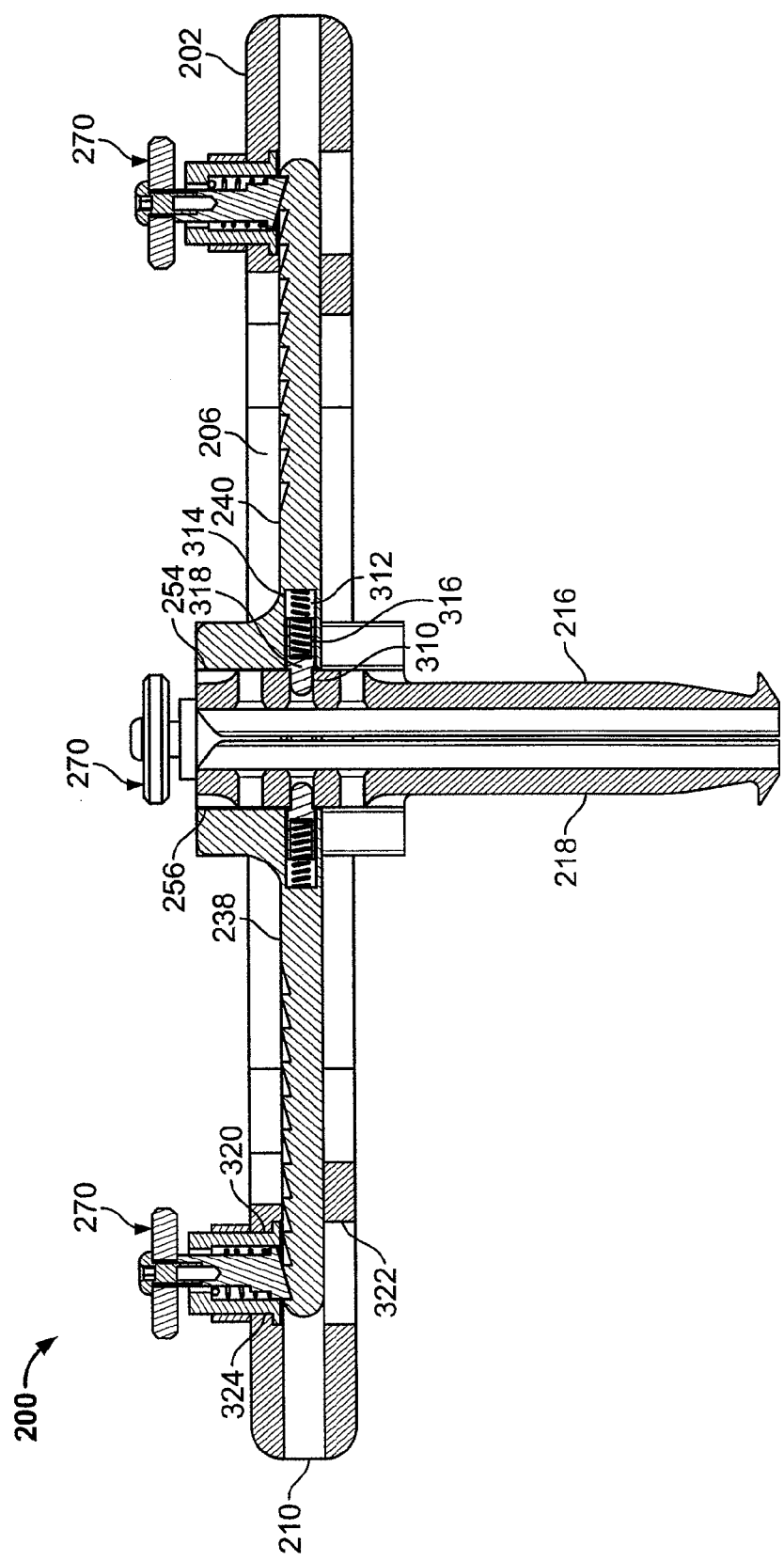
FIG. 17 is a cross-sectional view of the access retractor taken along line 17-17 of FIG. 16.

A plurality of through apertures 228 are formed through the blades 216, 218, 220 and 222 and are aligned with the dovetail recesses 262. The apertures 228 are configured to receive a locking pin 318 of the locking mechanism 310 of the sliders 238, 240, 242 and 244, as illustrated in FIG. 17. The locking pin 318 is partially received in a blind bore 314 of each of the sliders 238, 240, 242 and 244, and is biased outwardly therefrom by a compression spring 312 received in a bore 316 of the locking pin 318. The protruding tip of the pin 318 opposite its bore 316 is rounded and has a diameter sized to be received in the through apertures 228 of the blades 216, 218, 220 and 222 to restrict separation of the dovetail connections 254, 256, 258 and 260. To facilitate attachment of the blades 216, 218, 220 and 222 to their associated sliders 238, 240, 242 and 244, ramps 252 are formed adjacent the through apertures 228 to facilitate retraction of the locking pin 318 into the blind bore 314, and against the biasing force of the spring 312, until the locking pin 318 is aligned with one the through apertures 228, at which point the spring 312 will bias the top of the pin 318 into the through aperture 228 to restrict separation of the dovetail connection 254, 256, 258 and 260. The locking mechanism 310 can be released in the same manner discussed above with respect to the first embodiment. A plurality of longitudinally-aligned through apertures 228 are provided to permit the blades 216, 218, 220 and 222 to be positioned at different depths relative to the frame 202.

Figure 18:
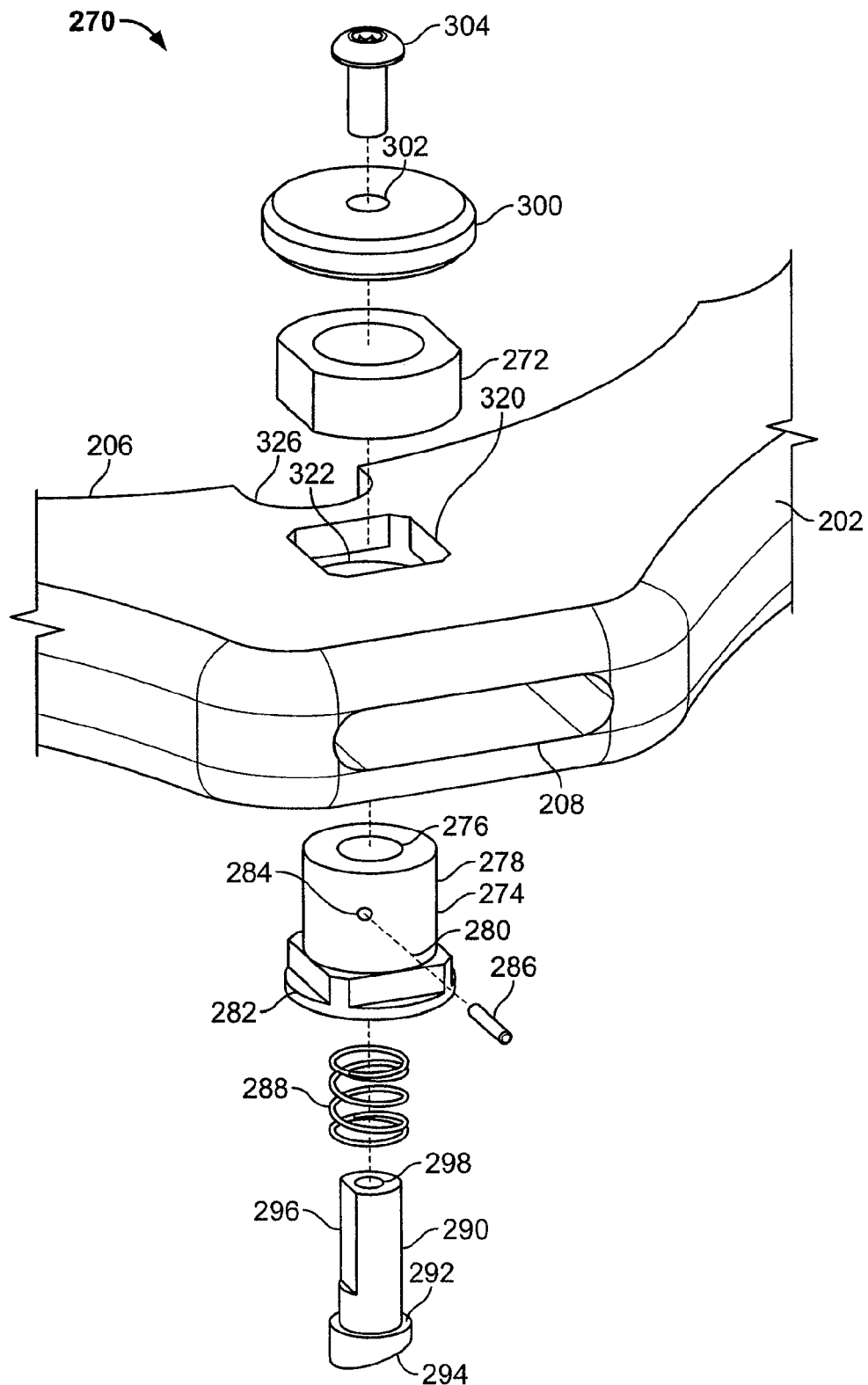
FIG. 18 is an exploded perspective view of a plunger assembly of the access retractor of FIG. 15.

Turning now to more of the details of the plunger assembly 270, the plunger assembly 270 includes a sleeve 274 having a radially extending flange 282, a cylindrical upper portion 278 and an intermediate polygonal portion 280, as illustrated in FIG. 18. The sleeve 274 along with the components depicted below the sleeve 274 in FIG. 18 have been rotated 90 degrees in relation to where they would otherwise be located to more fully show component features. A circular opening 322 extends partially through the frame 202 from the bottom thereof, as illustrated in FIG. 17, but stops at a distance between the slot 210 and the top of the frame 202. The circular opening 322 is sized to permit the radially extending flange 282 to fit therethrough. A polygonal opening 320 extends from the top of the frame 202 and intersects the circular opening 322, and corresponds in size to the polygonal portion 280 of the sleeve 274. The polygonal opening 320 is smaller than the circular opening 322 such that an interior ledge 324 is formed at the intersection of the polygonal opening 320 and the circular opening 322. The sleeve 274 is inserted into the circular opening 322 from the bottom of the frame 202. The intermediate polygonal portion 280 of the sleeve 274 mates with the corresponding polygonal opening 320 of the frame 202 in order to prevent rotation of the sleeve 274 relative to the frame 202.

The radially extending flange 282 engages the interior ledge 324 to limit extension of the sleeve 274 though the polygonal opening 320 in a direction extending outward from the frame 202 while permitting the cylindrical upper portion 278 of the sleeve 274 to protrude outwardly from the frame 202. A collar 272 is used to restrict movement of the sleeve 274 in a direction extending inward toward the frame 202. More specifically, the cylindrical upper portion 278 of the sleeve 274 has external threading that mates with internal threading of the collar 272. When the collar 272 is threadingly engaged with the cylindrical upper portion 278 of the sleeve 274, the sleeve 274 is held in position on the frame 202 by the collar 272, on the outer side of the frame 202, and the engagement between the flange 282 and the interior ledge 324 on the interior of the frame 202, while the polygonal portion 280 of the sleeve 274 and the corresponding polygonal opening 320 of the frame 202 prevent rotation of the sleeve 274.

A central bore 276 extends through the sleeve 274, and has a portion with a first diameter adjacent the upper end of the bore 276 and a portion with a second, larger diameter in the remainder of the sleeve 274. A plunger 290 is positioned within the central bore 276. The plunger 290 includes a shaft 295 with a diameter sized to fit through the portion of the central bore 276 of the sleeve 274 having the first diameter. The plunger 290 also includes an enlarged head 294 having a diameter greater than the portion of the central bore 276 having the first diameter of the sleeve 274 such that the shaft 295 but not the head 294 of the plunger 292 can protrude through the portion of the central bore 276 having the first diameter in order to retain the plunger 292 in the sleeve 274, as illustrated in FIG. 17.

A compression spring 288 is disposed in portion of the central bore 276 of the sleeve having the second, larger diameter. The spring 288 surrounds the shaft 295 of the plunger 290. One end of the spring is seated on a ledge 292 at the intersection of the shaft 295 and head 294 of the plunger 290, while the other end of the spring is seated at a ledge formed at the intersection of the first and second diameter portions of the central bore 276 of the sleeve 274. In this manner, the spring 288 biases the plunger 290, and in particular the head 294 of the plunger 290, relative to the sleeve 274 and inward into the circular opening 322 of the frame 202.

An end of the shaft 295 of the plunger 290, opposite the end having the head 294, protrudes through the portion of the central bore 276 of the sleeve 274 having the first diameter. The protruding end of the shaft 295 has a blind bore 298 with internal threading. A disc handle 300 is attached to the shaft 295 of the plunger 290 using a screw 304. The screw 304 extends through a bore 302 of the disc handle 300 and has external threading for mating with the internal threading of the blind bore 298 of the upper end of the shaft 295 of the plunger 290. The disc handle 300 can be grasped to pull the plunger 290, and in particular the head 294, outward relative to the circular opening 322 of the frame 202. The shaft 295 of the plunger 290 may optionally be shorted from that illustrated, along with the axial length of the sleeve 274, in order to form a lower profile access retractor.

The head 294 of the plunger 290 has an inclined ramp surface that is configured to engage the ratchet teeth 308 of the associated slider 238, 240, 242 or 244, as illustrated in FIG. 17. The ratchet teeth 308 include inclined surfaces corresponding to the inclined ramp surface of the head 294 of the plunger 290. The inclined surface of each of the ratchet teeth 308 is orientated such that the slider 238, 240, 242 or 244 is permitted to retract, but is blocked by the plunger 290 from moving inward relative to the opening 204 of the frame 202 unless the plunger 290 is shifted to its unengaged position using the disc handle 300.

More specifically, a ledge of each of the ratchet teeth 308 is positioned to abut against the head 294 of the plunger 290 when the head 294 of the plunger 290 is biased by the spring 288 against the slider 238, 240, 242 or 244. The engagement between the ledge of the ratchet teeth 308 and the head of the plunger 294 restricts the slider from moving inward relative to the opening 204 of the frame 202 and toward the extended position. However, the engagement between the inclined ramp surface of the head 294 of the plunger 290 and the inclined surface of the ratchet teeth 308 function to shift the plunger 290 to its unlocked position, against the biasing force of the spring 288, when the slider 238, 240, 242 or 244 is moved toward its retracted position. As the slider 238, 240, 242 or 244 is moved toward its retracted position, the engagement between the inclined ramp surface of the head 294 of the plunger 290 and the inclined surface of the ratchet teeth 308 cycles the plunger 290 between its locked and unlocked positions as it passes each ratchet tooth 308, thereby providing a plurality of discrete positions of the slider 238, 240, 242 or 244 where movement toward the extended position, and inward relative to the opening 204 of the frame 202, is restricted.

A pin 286 is used to restrict rotation of the plunger 290 in the sleeve 274, and to maintain the inclined ramp surface of the head 294 of the plunger 290 in proper alignment with the inclined surfaces of the ratchet teeth 308 of the associated sliders 238, 240, 242 and 244. The pin 286 is positioned in a aperture 284 extending transversely through the sleeve 274. The aperture 284 intersects the central bore 276 of the sleeve 274, such that an intermediate portion of the pin 286 is disposed in the central bore 276. The intermediate portion of the pin 286 abuts a flat 296 formed on the shaft 295 of the plunger 290 to restrict rotation of the plunger 290 relative to the sleeve 274, and thereby to maintain the inclined ramp surface of the head 294 of the plunger in the orientation corresponding to the orientation of the inclined surfaces of the ratchet teeth 308 of the associated slider 238, 240, 242 or 244.

The frame 202 may be formed from a carbon-fiber material, and in particular from a carbon-filled PEAK. The sliders 238, 240, 242 and 244 and blades 216, 218, 220 and 222 may be formed from anodized titanium nitrate. Preferably, all of the components of the access retractor 200 can be readily disassembled and are suitable for sterilization, such as in an autoclave.

Figure 34:
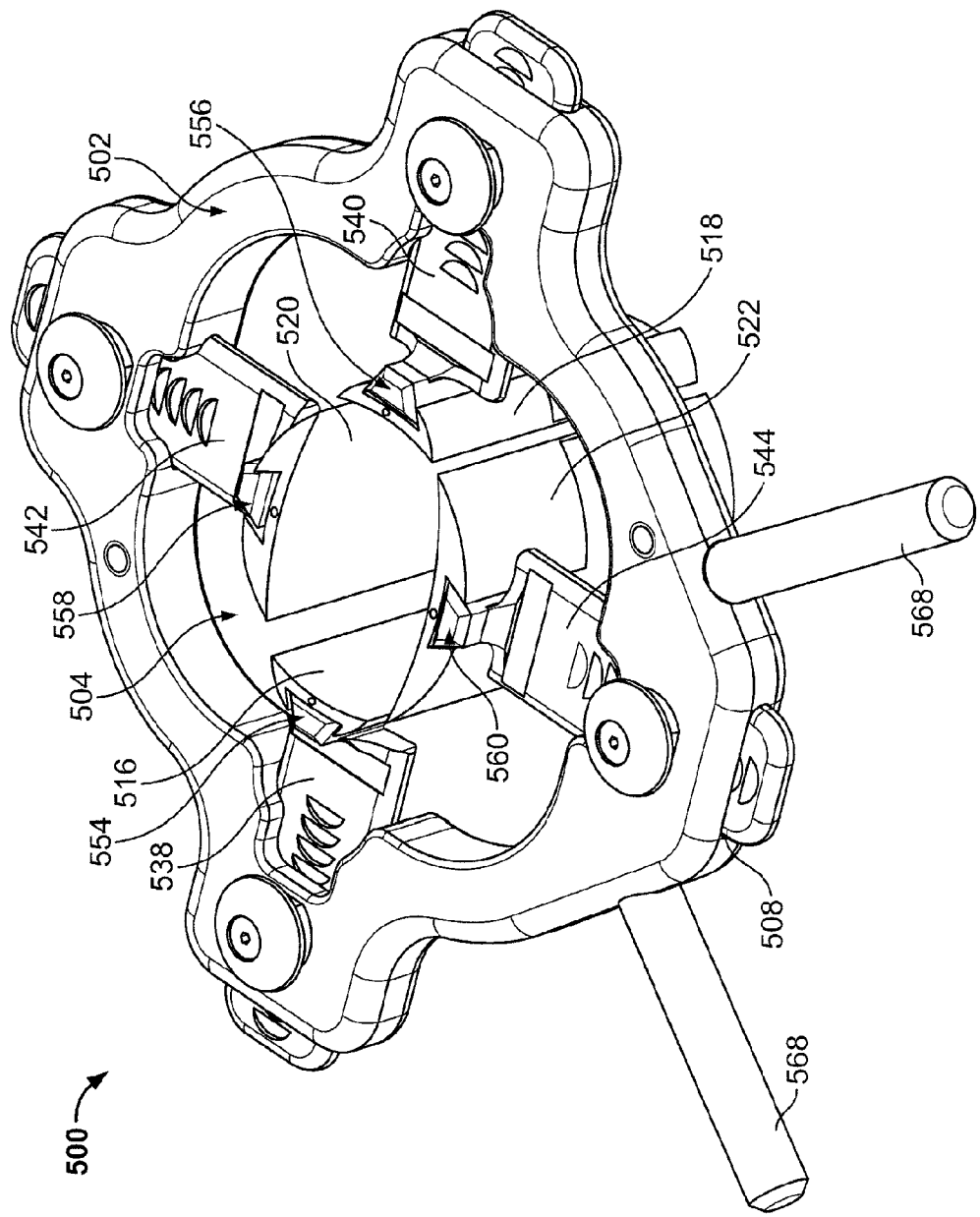
FIG. 34 is a perspective view of a third embodiment of an access retractor showing an enlarged access opening.

Turning now to another embodiment, the access retractor 500 of FIG. 34 comprises a generally planar body or frame 502 having an opening 504. However, while openings 14 and 204 are generally oblong or ovular, the access opening 504 defined by the retractor frame 502, has a length that is generally equal to its width. As shown, the workspace within frame 502 is increased by having the larger opening 504 as compared to the workspace provided in retractors 10 and 200. In addition, minimizing the radii in the corners of the inside edge of the frame 502 increases area in the opening without significantly increasing the size of the frame 502 thereby providing the surgeon improved access. In other words, a square access opening, while contemplated, is not as desirable as an access opening with curved corners. In this instance, minimizing the radii of these slightly curved corners removes material of the frame to maximize the area of the opening.

Like retractor 200, retractor 500 has four blades 516, 518, 520, and 522 each of which is attached to a ratcheting sliders 538, 540, 542, and 544. These sliders can be locked into position with ratcheting mechanisms, such as the type disclosed above with respect to the embodiments of FIGS. 1-33. The sliders 538, 540, 542, and 544 are disposed in four slots 508 that are spaced a relatively equal distant apart and arranged 90° from one another. Sliders 538, 540, 542, and 544 have dovetail connections 554, 556, 558, and 560 which are configured to releasably attach the blades 516, 518, 520, and 522. The radius of curvature of the four dovetail connections is relatively equal such that the four blades are interchangeable. Thus, a surgeon can attach any of the blades to any of the dovetail connections. Such interchangeability provides a surgeon with the additional flexibility.

The retractor 500 preferably includes three blade widths: 18 mm, 32 mm, and 42 mm. The blades have a variety of lengths from 40 mm to 100 mm in 10 mm increments. The blades chosen for use during a particular procedure depend on the patient, the type of procedure, and surgeon preference. In one preferred embodiment, the retractor 500 will be accompanied by four 18 mm blades of every length from 40 mm to 100 mm. Thus, if desired a surgeon can create a more square working area at the surgical site by attaching four blades of equal width. Along with the four 18 mm blades, two 32 mm blades of every length will be included and one 42 mm blade will be included with the access retractor 500. Thus, with retractor 500, it is contemplated that different blade widths will be used across from one another. For example, during the first retraction step, a surgeon may employ two 18 mm blades of 50 mm length opposite one another, then during the second step, the surgeon may use a 32 mm width blade and a 42 mm width blade. Such a configuration is shown in FIG. 34. Having unequal blades directly opposite one another creates space in the retractor 500 such that surgical tools may be employed in a manner so as not to be obstructed by the blades. During procedures requiring access to the spine, the 42 mm blades may be used adjacent to the spine and the shorter blades opposite thereto, allowing surgeons to employ tools in a more flexible manner with a smaller blade opposite the 42 mm blade. While using such a configuration does create a gap between some of blades thereby allowing for possible encroachment of tissue or blood, such a gap may be necessary to provide the surgeon with adequate workspace. Further, the retractor includes blades having a variety of widths and lengths that can be attached to any of the dovetail connection and this allows the surgeon to create a gap in one particular area without having to create any unnecessary gaps.

In another aspect of the invention, the access retractor 500 has the mounting members located on adjacent sides of the retractor as shown in FIG. 34. With the mounting members 568 in this configuration, the surgeon may tilt the retractor while within the patient without one of the mounting members adversely abutting the patient's skin adjacent to the surgical site.

Figure 35:
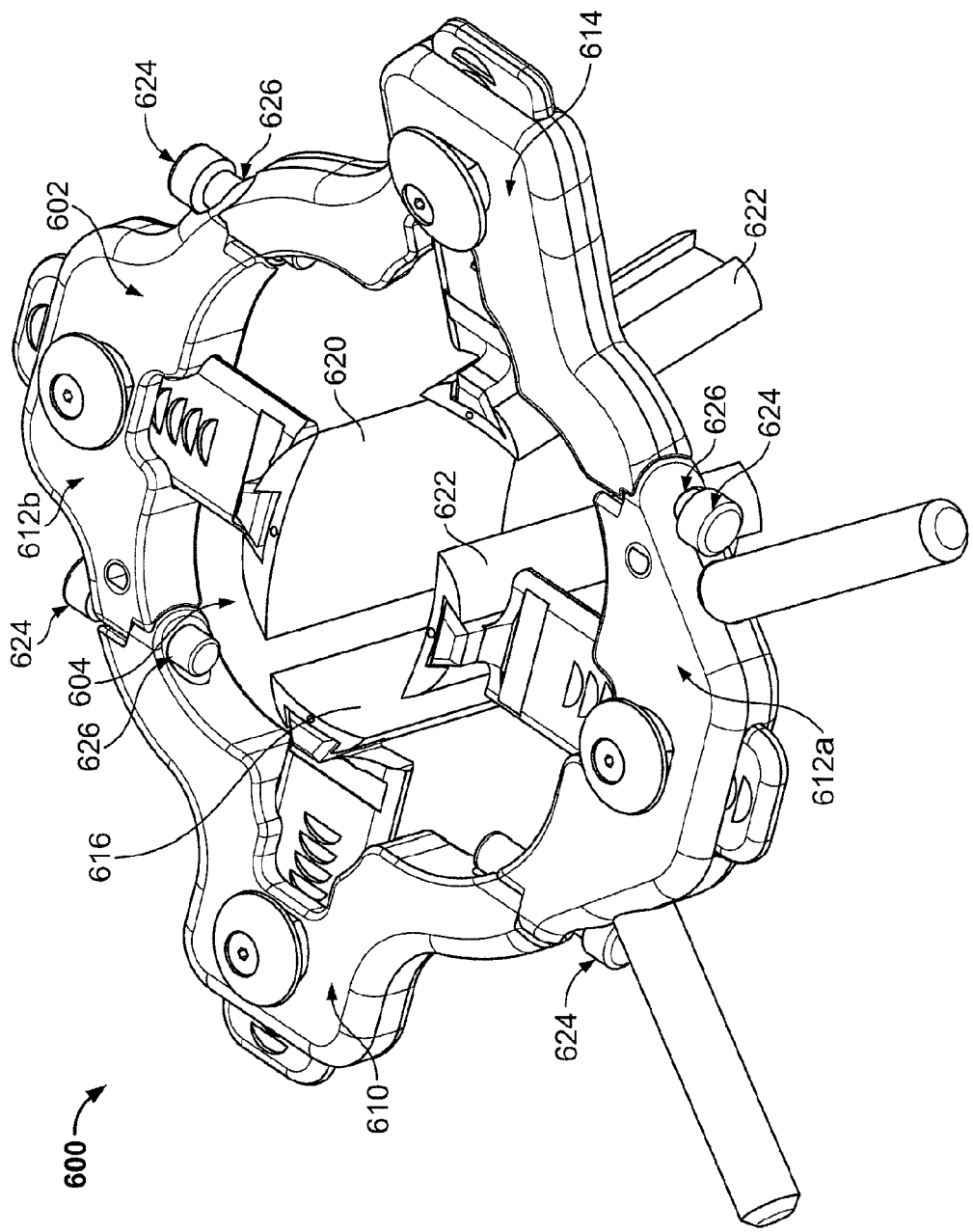
FIG. 35 is a perspective view of a fourth embodiment of an access retractor showing a retractor frame having an articulated section.

Turning now to another embodiment, the access retractor 600 of FIG. 35 has an articulated body. More specifically, retractor 600 comprises a generally planar body 602 and has an opening 604 similar to that shown in FIG. 34, however, the body 602 has end sections 610 and 614 that are hingedly attached to mid-sections 612*a* and 612*b* via pivot connections therebetween. The end-sections 610, 614 move relative to the mid-sections 612*a*, 612*b*, which are stationary relative to one another. By having sections that can be pivoted relative to one another, the retractor can be adjusted from a relatively planar profile to a profile that more closely corresponds to the contours of the patient's body.

The pivot connections between the sections may be a shoulder bolt. In one example, pins, screws, or bolts 624 may join the frame sections together while permitting the sections to articulate relative to one another. Bolts 624 are disposed through an aperture or opening 626. The opening 626 includes an internally smooth through bore, which is aligned with an internally threaded though bore. The bolt 624 has a bolt head, a threaded end, and an intermediate section. The internally smooth through bore is located in sections 612*a* and 612*b* and the internally threaded though bore is located in section 610 and 614. Thus, the sections 610, 612*a*, 612*b*, and 614 are moveable with respect to one another.

Retractor 600 may also have a locking mechanism to hold the sections 610, 612*a*, 612*b*, and 614 relative to one another after the surgeon has positioned the retractor 600 for use during the surgical procedure. Such a locking mechanism may be any of a number such mechanisms known in the art such as a detent mechanism, linearly inserted locking structure, a ratchet, or a clamp. The locking mechanism may be provided on one or both of the pivot connections for each sections.

As shown in FIG. 35, retractor 600 has four blades 616, 618, 620, and 622. The blades 616, 618, 620, and 622 are of equal width. Like retractor 10, 200 and 500, the blades are attached to ratcheting sliders 638, 640, 642, and 644. These sliders are disposed in four slots 608. In FIG. 35 retractor 600 has four blades of relatively equal width and three of those blades 616, 618, and 620 have a relatively equal length, however blade 620 is longer than the other three blades. Having a blade longer than the others may be helpful depending on the patient's anatomy or the procedure. As shown in FIG. 35, section 614 is articulated at an angle such that blade 622 is shown angled outward. As suggested above with differing blade lengths, depending on the procedure, patient, and surgeon preference, such a configuration with an angled opening may provide the surgeon with much needed workspace within the incision.

Although various features are discussed with respect to multiple embodiments, it is understood that the features can be interchangeable among the embodiments. While there have herein been illustrated and described with respect to specific examples and embodiments, including presently preferred modes of carrying out the invention, those skilled in the art will appreciate that there are numerous variations and permutations of the above-described apparatus and methods that fall within the scope and spirit of the invention as set forth in the appended claims.

What is claimed is:

1. A method of enlarging an incision, the method comprising:
inserting a first pair of opposing tissue engaging members into the incision;
connecting the first pair of tissue engaging members to initial stage operating mechanisms of a retractor;
retracting the first pair of tissue engaging members away from each other to enlarge the incision to form an intermediate size opening;
positioning mounting portions of subsequent stage operating mechanisms of the retractor above the intermediate size opening after retracting the first pair of tissue engaging members to form the intermediate size opening;
inserting a second pair of opposing tissue engaging members in a downward direction into the intermediate size opening after positioning the mounting portions of the subsequent stage operating mechanisms above the intermediate size opening; and
sliding attachment portions of the second pair of tissue engaging members in the downward direction onto the mounting portions of the subsequent stage operating mechanisms as the second pair of tissue engaging members are inserted into the intermediate size opening after positioning the mounting portions of the subsequent stage operating mechanisms above the intermediate size opening to connect the second pair of tissue engaging members to the subsequent stage operating mechanisms.

2. The method of claim 1, further comprising retracting the second pair of tissue engaging members away from each other to enlarge the intermediate size opening to form a final size opening.

3. The method of claim 2, wherein the step of retracting the first pair of tissue engaging members includes restricting movement of the first pair of tissue engaging members toward each other, and wherein the step of retracting the second pair of tissue engaging members includes restricting movement of the second pair of tissue engaging members toward each other.

4. The method of claim 1, wherein the step of retracting the first pair of tissue engaging members further comprises enlarging the incision from an initial width less than a width of the second pair of tissue engaging members to an intermediate width into which the second pair of tissue engaging members can be inserted.

5. A method of enlarging an incision, the method comprising:
inserting a first pair of tissue engaging members into the incision;
retracting the first pair of tissue engaging members apart from each other to enlarge the incision to an intermediate size opening;
advancing a mounting portion of a retractor operating mechanism to an extended position above the intermediate size opening;
advancing a tissue engaging member between the first pair of tissue engaging members in a downward direction into the intermediate size opening;
sliding the tissue engaging member in the downward direction along the mounting portion of the retractor operating mechanism in the extended position as the tissue engaging member is advanced between the first pair of tissue engaging members to connect the tissue engaging member to the mounting portion of the extended retractor operating mechanism; and retracting the mounting portion of the retractor operating mechanism and the tissue engaging member connected thereto to further enlarge the incision to a larger size opening than the intermediate size opening.

6. The method of claim 5 further comprising sliding a second tissue engaging member in the downward direction along another retractor operating mechanism to connect the second tissue engaging member to the other retractor operating mechanism after retracting the first pair of tissue engaging members apart from each other to enlarge the incision to the intermediate size opening.

7. The method of claim 5 wherein sliding the tissue engaging member in the downward direction along the mounting portion of the retractor operating mechanism to connect the tissue engaging member to the mounting portion of the retractor operating mechanism includes engaging a slide connection between the tissue engaging member and the mounting portion of the retractor operating mechanism.

8. The method of claim 5 further comprising:
inserting a dilation tool into the incision; and
sliding the first pair of tissue engaging members along the dilation tool and into the incision.

9. The method of claim 8 further comprising removing the dilation tool from the incision while the first pair of tissue engaging members remains disposed in the incision.

10. The method of claim 5 wherein each of the tissue engaging members of the first pair of tissue engaging members has a predetermined width and the tissue engaging member advanced between the first pair of tissue engaging members has a predetermined width greater than the predetermined widths of the first pair of tissue engaging members.

11. The method of claim 5 further comprising pivoting a portion of a retractor frame to angle one of the tissue engaging members of the first pair relative to the other tissue engaging member of the first pair and the tissue engaging member advanced between the first pair of tissue engaging members.

12. The method of claim 5 wherein the advancing the tissue engaging member comprises advancing the tissue engaging member and another tissue engaging member between the first pair of tissue engaging members and into the intermediate size opening.

13. The method of claim 12 further comprising connecting the other tissue engaging member advanced between the first pair of tissue engaging members to a mounting portion of another retractor operating mechanism; and
wherein retracting the mounting portion of the retractor operating mechanism and the tissue engaging member connected thereto includes retracting the mounting portions of the retractor operating mechanisms to retract the tissue engaging members advanced between the first pair of tissue engaging members apart from each other to enlarge the incision to a final size opening.

14. The method of claim 13 wherein retracting the first pair of tissue engaging members apart from each other includes retracting the first pair of tissue engaging members along a first direction, and wherein retracting the tissue engaging members advanced between the first pair of tissue engaging members apart from each other includes retracting the tissue engaging members advanced between the first pair of tissue engaging members along a second direction transverse to the first direction.

15. The method of claim 5 further comprising connecting the first pair of tissue engaging members to retractor operating mechanisms and inserting the first pair of tissue engaging members into the incision while keeping the first pair of tissue engaging members connected to the respective retractor operating mechanisms.

16. The method of claim 5 wherein inserting the first pair of tissue engaging members into the incision comprises advancing tapered leading end portions of the first pair of tissue engaging members that are configured to urge tissue outwardly relative to the first pair of tissue engaging members as the first pair of tissue engaging members are inserted into the incision.

17. The method of claim 5 further comprising positioning the first pair of tissue engaging members adjacent the incision in a generally parallel orientation relative to each other; and
wherein inserting the first pair of tissue engaging members into the incision comprises inserting the first pair of tissue engaging members into the incision while maintaining the generally parallel orientation of the first pair of tissue engaging members relative to each other.

* * * * *